US009884074B2

(12) United States Patent
Cooper et al.

(10) Patent No.: US 9,884,074 B2
(45) Date of Patent: *Feb. 6, 2018

(54) BI-FUNCTIONAL CO-POLYMER USE FOR OPHTHALMIC AND OTHER TOPICAL AND LOCAL APPLICATIONS

(71) Applicant: Eyeon Particle Sciences LLC, Rochester, NY (US)

(72) Inventors: Eugene Rex Cooper, Berwyn, PA (US); David Maxwell Kleinman, Rochester, NY (US); Andrew Loxley, Philadelphia, PA (US); Mark A. Mitchnick, East Hampton, NY (US)

(73) Assignee: Eyeon Particle Sciences LLC, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,188

(22) Filed: Mar. 14, 2016

(65) Prior Publication Data

US 2016/0243156 A1  Aug. 25, 2016

Related U.S. Application Data

(63) Continuation of application No. 14/661,804, filed on Mar. 18, 2015, now Pat. No. 9,283,248, which is a continuation of application No. 14/328,484, filed on Jul. 10, 2014, now Pat. No. 9,005,596, which is a continuation of application No. 12/708,329, filed on Feb. 18, 2010, now Pat. No. 8,802,075.

(60) Provisional application No. 61/153,416, filed on Feb. 18, 2009.

(51) Int. Cl.
| | |
|---|---|
| *A61K 31/785* | (2006.01) |
| *A61K 9/00* | (2006.01) |
| *A61K 9/51* | (2006.01) |
| *A61K 31/74* | (2006.01) |
| *A61K 47/34* | (2017.01) |
| *A61K 35/02* | (2015.01) |
| *A61K 31/765* | (2006.01) |
| *A61K 45/06* | (2006.01) |
| *G02C 7/04* | (2006.01) |
| *A61K 9/50* | (2006.01) |
| *A61K 31/045* | (2006.01) |
| *A61K 31/7036* | (2006.01) |

(52) U.S. Cl.
CPC .......... *A61K 31/785* (2013.01); *A61K 9/0019* (2013.01); *A61K 9/0043* (2013.01); *A61K 9/0048* (2013.01); *A61K 9/0051* (2013.01); *A61K 9/0073* (2013.01); *A61K 9/5031* (2013.01); *A61K 9/5146* (2013.01); *A61K 31/045* (2013.01); *A61K 31/7036* (2013.01); *A61K 31/74* (2013.01); *A61K 31/765* (2013.01); *A61K 35/02* (2013.01); *A61K 45/06* (2013.01); *A61K 47/34* (2013.01); *G02C 7/04* (2013.01)

(58) Field of Classification Search
CPC .. A61K 31/785; A61K 9/0043; A61K 9/0048; A61K 9/0051; A61K 9/5146; A61K 31/74; A61K 47/34; A61K 35/02; A61K 31/765; A61K 45/06; A61K 9/0019; A61K 9/0073; A61K 9/5031; A61K 31/045; A61K 31/7036; G02C 7/04
See application file for complete search history.

(56) References Cited

U.S. PATENT DOCUMENTS

| | | | |
|---|---|---|---|
| 5,232,984 A | 8/1993 | Hubbell et al. | 525/54.1 |
| 5,380,536 A | 1/1995 | Hubbell et al. | 424/497 |
| 5,462,990 A | 10/1995 | Hubbell et al. | 525/54.1 |
| 5,567,440 A | 10/1996 | Hubbell et al. | 424/484 |
| 5,607,698 A * | 3/1997 | Martin | A61K 9/0048 424/613 |
| 5,627,233 A | 5/1997 | Hubbell et al. | 525/54.1 |
| 5,820,882 A | 10/1998 | Hubbell et al. | 424/491 |
| 5,849,839 A | 12/1998 | Hubbell et al. | 525/54.1 |
| 6,037,328 A | 3/2000 | Hu et al. | 514/23 |
| 6,231,892 B1 | 5/2001 | Hubbell et al. | 424/491 |
| 6,350,527 B1 | 2/2002 | Hubbell et al. | 428/473 |
| 6,596,267 B1 | 7/2003 | Hubbell et al. | 424/78.26 |
| 6,652,902 B2 | 11/2003 | Hubbell et al. | 427/2.11 |
| 6,732,521 B2 | 5/2004 | Otake | 428/500 |
| 6,958,148 B1 | 10/2005 | Green et al. | 424/94.5 |

(Continued)

FOREIGN PATENT DOCUMENTS

| | | | |
|---|---|---|---|
| AU | 683312 B2 | 11/1997 | C08G 81/00 |
| AU | 761903 B2 | 3/2000 | |

(Continued)

OTHER PUBLICATIONS

Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Neeraj Kumar, et al, Polyanhydrides: An Overview, 54 Adv. Drug Del. Rev. 889 (2002).*
Michael J. Doughty, Re-wetting, Comfort, Lubricant and Moisturizing Solutions for the Contact Lens Wearer, 22 Cont. Lens Ant. Eye, 116 (1999).*
Baumeler, Susan, "Sugar Adsorption on PLL-g-PEG-coated $Nb_2O_5$ Surfaces," ETH Zurich Laboratory for Surface Science and Technology, pp. 1-30, Jun. 2004.

(Continued)

*Primary Examiner* — Sean M Basquill
(74) *Attorney, Agent, or Firm* — Sunstein Kann Murphy & Timbers LLP

(57) ABSTRACT

The invention contemplates a copolymer which is a graft or block copolymer useful to change wettability and surface characteristics of biological surfaces. Methods for use of these formulations and coatings to change wettability and sterically stabilize, and lubricate biological surfaces in a subject, for example, in the treatment of dry eye syndrome, and to prevent adherence of unwanted proteins, for example in the treatment of contact lens intolerance, are provided.

19 Claims, 5 Drawing Sheets

(56) References Cited

U.S. PATENT DOCUMENTS

| | | | |
|---|---|---|---|
| 7,029,688 B2* | 4/2006 | Hubbell | A61K 31/77 424/422 |
| 7,316,845 B2* | 1/2008 | Hubbell | A61L 27/34 427/2.24 |
| 8,802,075 B2* | 8/2014 | Cooper | A61K 9/0043 424/78.17 |
| 9,005,596 B2* | 4/2015 | Cooper | A61K 9/0043 424/78.04 |
| 9,283,248 B2* | 3/2016 | Cooper | A61K 9/0043 |
| 2002/0114778 A1 | 8/2002 | Xia et al. | 424/78.38 |
| 2005/0202097 A1 | 9/2005 | Maskin | 424/524 |
| 2006/0052340 A1 | 3/2006 | Tsuzuki et al. | 514/57 |
| 2006/0083781 A1 | 4/2006 | Shastri et al. | 424/450 |
| 2006/0094643 A1 | 5/2006 | Svirkin et al. | 514/8 |
| 2006/0122290 A1 | 6/2006 | Hubbell et al. | 523/113 |
| 2007/0154521 A1 | 7/2007 | Zhao | 424/426 |
| 2007/0203039 A1* | 8/2007 | Borazjani | A61L 12/143 510/112 |
| 2009/0264538 A1 | 10/2009 | Hubbell et al. | 514/772.2 |

FOREIGN PATENT DOCUMENTS

| | | | |
|---|---|---|---|
| CA | 2 173 317 A1 | 4/1995 | A61K 9/50 |
| CA | 2 286 590 | 10/1998 | C08G 81/00 |
| CA | 2 341 519 | 3/2000 | A61L 31/08 |
| CN | 1644215 A | 7/2005 | A61K 47/34 |
| EP | 0 553 195 B1 | 8/1993 | A61K 9/50 |
| EP | 0 722 470 B1 | 7/1996 | C08G 81/00 |
| EP | 1 009 451 B1 | 10/2003 | A61L 31/00 |
| EP | 1 107 802 B1 | 10/2004 | A61L 31/08 |
| WO | WO 1998/47948 | 10/1998 | C08G 81/00 |
| WO | WO 1999/10022 | 3/1999 | A61L 31/00 |
| WO | WO 2004/004744 A1 | 1/2004 | A61K 31/715 |
| WO | WO 2006/039467 A2 | 4/2006 | A61L 27/18 |
| WO | WO 2006/083781 A1 | 4/2006 | 424/450 |
| WO | WO 2008/137066 A1 | 11/2008 | A61K 9/127 |
| WO | WO 2009/084069 A2 | 7/2009 | |

OTHER PUBLICATIONS

Benelli, Umbergo, "Systane® Lubricant Eye Drops in the Management of Ocular Dryness," Clinical Ophthalmology, vol. 5, pp. 783-790, Jun. 2011.
Billinger, Michael et al., "Polymer stent Coating for Prevention of Neointimal Hyperplasia," Original Contributions, Abstract, 1 page.
Binkert, Andreas, et al., "Covalent Immobilization of PLL-g-PEG onto Silicone Hydrogel Contact Lenses,"AB Idealeague, 1 page, 2006.
Blättler, Thomas, et al, "High Salt Stability and Protein Resistance of Poly(l-lysine)-g-poly(ethylene glycol) Copolymers Covalently Immobilized via Aldehyde Plasma Polymer Interlayers on Inorganic and Polymeric Substrates," Langmuir, vol. 22, No. 12, pp. 5760-5769, May 2006.
Bron, Anthony J., "Diagnosis of Dry Eye," Survey of Ophthalmology, vol. 45, Supplement 2, pp. S221-S226, Mar. 2001.
Doughty, Michael J., "Re-Wetting, Comfort, Lubricant and Moisturising Solutions for the Contact Lens Wearer," Contact Lens and Anterior Eye, vol. 22, Issue 4, pp. 116-126, 1999.
Drobek, Tanja, et al, "Nanotribology of Surface-Grafted PEG Layers in an Aqueous Environment," ETH Zurich, Laboratory for Surface Science Technology, Department of Materials, Langmuir pp. A-E, Sep. 5, 2007.
Elbert, Donald L., et al. "Self-Assembly and Steric Stabilization at Heterogeneous, Biological Surfaces Using Adsorbing Block Copolymers," Chemistry & Biology, vol. 5, Issue 3, pp. 177-183, Mar. 1998.
Fink, Jenny, et al., "Comparative Study and Improvement of Current Cell Micro-Patterning," Lab Chip, vol. 7, pp. 672-670, Apr. 2007.

Gensheimer, David, et al., "Novel Formulation of Glycerin 1% Artificial Tears Extends Tear Film Break-Up Time Compared With Systane Lubricant Eye Drops," Journal of Ocular Pharmacology, vol. 28, No. 5, Oct. 28, 2012.
Germainier, Yves, et al. "Enhanved Bone Appositin Around Biofunctionalized Sanblasted and Acid-Etched Titanium Implants Surfaces. A Histomorphometric Study in Miniature Pigs," Clinical Oral Implants Research, vol. 17, No. 3, pp. 251-257, Jun. 2006.
Gonzalez-Lopez, Jaime, et al., "Self-associative behavior and drug-solubilizing ability of poloxamine (tetronic) block copolymers," Langmuir, vol. 24, No. 19, pp. 10688-10697, Oct. 7, 2008.
Hague, Tasima, et al., "Superior Cell Delivery Features of Poly-(ethylene glycol) Incorporated Alginate, Chitosan, and Poly-l-lysine Microcapsules," Molecular Pharmaceutics, vol. 2, No. 1, pp. 29-36, 2005.
Harris, L.G., et al., "*Staphylococcus aureus* adhesion to titanium oxide surfaces coated with non-functionalized and peptide-functionalized poly(l-lysine)-grafted-poly(ethylene glycol) copolymers," Biomaterials, vol. 25, Issue 18, pp. 4135-4148, Aug. 2004.
Hansson, Kenny M., et al., "Whole blood coagulation on protein adsorption-resistant PEG and peptide functionalised PEG-coated titanium surfaces," Biomaterials, vol. 26, Nov. 8, pp. 861-872, Mar. 2005.
Huang, Ning-Ping, et al., "Poly(L-lysine)-g-poly(ethylene glycol) Layers on Metal Oxide Surfaces: Surface-Analytical Characterization and Resistance to Serum and Fibrinogen Adsorption," Laboratory for Surface Science and Technology and Institute for Biomedical Engineering, Langmuir, vol. 17, No. 2, pp. 489-498, 2001.
Kumar, Neeraj, et al., "Polyanhydrides: An Overview," Advance Drug Delivery Reviews, vol. 54, No. 7, pp. 889-910, Oct. 16, 2002.
Kurrat, Roger, "Adsorption of Biomolecules on Titanium Oxide Layers in Biological Model Solutions," Swiss Federal Institute of Technology Zurich, Dissertation ETH Nr. 12891, 103 pages, 1998.
Lee, Seunghwan, et al., "Adsorption and Lubricating Properties of Poly(L-Lysine)-Graft-Poly(Ethylene Glycol) on Human-Hair Surfaces," ACS Applied Materials & Interfaces, vol. 1, No. 9, pp. 1938-1945, Sep. 2009.
Lee, Seunghwan, et al., "An Aqueous-Based Surface Modification of Poly(Dimethylsiloxane) With Poly(Ethylene Glycol) to Prevent Biofouling," Langmuir, vol. 21, No. 25, pp. 11957-11962, Dec. 6, 2005.
Lemp, Michael A., et al., The Definition and Classification of Dry Eye Disease: Guidelines from the International Dry Eye WorkShop, The Ocular Surface, vol. 5, No. 2, 6 pages, Apr. 2007.
Li, Shyh-Dar, et al., "Pharmacokinetics and Biodistribution of Nanoparticles," Molecular Pharmaceutics, vol. 5, No. 4, pp. 496-504, 2008.
Maddikeri, RR., et al., "Bacterial Adhesion to PLL-g-PEG Modified Surfaces," European Cells and Materials, vol. 13, Supplement 2, p. 70-71, 2007.
Maddikeri, R.R., et al., "Reduced Medical Infection Related Bacterial Strains Adhesion on Bioactive RGD Modified Titanium Surfaces: A First Step Toward Cell Selective Surfaces," Wiley InterScience, Journal of Biomedical Materials Research, Part A, vol. 84, No. 2, pp. 425-435, Feb. 2008.
Marie, Rodolphe, et al., "Use of PLL-g-PEG in Micro-Fluidic Devices for Localizing Selective and Specific Protein Binding," Langmuir, vol. 22, No. 24, pp. 10103-10108, Nov. 21, 2006.
Morgenthaler, Sara, et al., "Poly(L-Lysine)-Grafted-Poly(Ethylene Glycol)-Based Surface-Chemical Gradients. Preparation, Characterization, and First Applications," Biointerphases, vol. 1, No. 4, pp. 156-165, Dec. 2006.
Nalam, Prathima C., et al., "Macrotribological Studies of Poly(L-lysine)-graft-Poly(ethylene glycol) in Aqueous Glycerol Mixtures," Tribology Letters, vol. 37, Issue 3, pp. 541-552, Mar. 2010.
Nicolson, Paul C., et al., "Soft Contact Lens Polymers: An Evolution," Biomaterials, Ophthalmic Special Edition, vol. 22, Issue 24, pp. 3273-3283, Dec. 15, 2001.
Ousler, George W., et al., "An Evaluation of Tear Film Break up Time extension and Ocular Protection Index Scores Among Three Marketed Lubricant Eye Drops," Cornea, vol. 26, No. 8, pp. 949-952, Sep. 2007.

(56) References Cited

OTHER PUBLICATIONS

Pasche, Stéphanie, et al., "Compression of Adsorbed Poly(L-Lysine)-G-Poly(Ethylene Glycol) Measured by AFM," European Cells and Materials, vol. 6, Supplement 1, p. 44, 2003.
Pasche, Stéphanie, et al., "Poly(L-lysine)-graft-poly(ethylene glycol) Assembled Monolayers on Niobium Oxide Surfaces: A Quantitative Study of the Influence of Polymer Interfacial Architecture on Resistance to Protein Adsorption by ToF-SIMS and in Situ OWLS," Langmuir, vol. 19, No. 22, pp. 9216-9225, 2003.
Patani, George A., et al., "Bioisosterism: A Rational Approach in Drug Design," Chemical Reviews, vol. 96, No. 8, pp. 3147-3176, Dec. 19, 1996.
Rossetti, Fernando F., et al., "Interaction of poly(L-lysine)-g-poly(ethylene glycol) with supported phospholipid bilayers," Biophysical Journal, vol. 87, No. 3, pp. 1711-1721, Sep. 2004.
Ruiz-Taylor, L.A., et al., "Monolayers of derivatized poly(l-lysine)-grafted poly(ethylene glycol) on metal oxides as a class of biomolecular interfaces," Proceedings of the National Academy of Sciences of the United States of America, vol. 908, No. 3, pp. 852-857, Jan. 30, 2001.
Sato, Ayumi, et al, "Polymer Brush-Stabilized Polyplex for a siRNA Carrier With Long Circulatory Half-Life," Journal of Controlled Release, vol. 122, No. 3, pp. 209-216, Oct. 8, 2007.
Schuler, Martin, et al. "Biomimetic Modification of Titanium Dental Implant Model Surfaces Using The RGDSP-Peptide Sequence: A Cell Morphology Study," Biomaterials, vol. 27, No. 21, pp. 4003-4015, 2006.
Simmons, Peter A., et al., "Clinical Performance of a Mid-Viscosity Artificial Tear for Dry Eye Treatment," Cornea, vol. 26, No. 3, pp. 294-302, Apr. 2007.
Sawhney, Amarpreet S., et al., "Poly(ethylene oxide)-graft-poly(L-lysine) copolymers to enhance the biocompatibility of poly(L-lysine)-alginate microcapsule membranes," Biomaterials, vol. 12, Issue 12, pp. 863-870, 1992.
Torigoe, Hidetaka, et al., "Poly(L-lysine)-Graft-Dextran Copolymer Promotes Pyrimidine Motif Triplex DNA Formation at Physiological pH," The Journal of Biological Chemistry, vol. 274, No. 10, pp. 6161-6167, Mar. 1999.
Tosatti, S., et al., "Peptide functionalized poly(L-lysine)-g-poly(ethylene glycol) on titanium: resistance to protein adsorption in full heparinized human blood plasma," Biomaterials, vol. 24, No. 27, pp. 4949-4958, Dec. 2003.

Vandamme, Th.F., "Microemulsions as Ocular Drug Delivery Systems: Recent Developments and Future Challenges," Progress in Retinal and Eye Research, vol. 21, Issue 1, pp. 15-34, Jan. 2002.
VandeVondele, Stephanie, et al., "RGD-Grafted Poly-L-Lysine-graft-(Polyethylene Glycol) Copolymers Block Non-Specific Protein Adsorption While Promoting Cell Adhesion," Biotechnology and Bioengineering, vol. 82, No. 7, pp. 784-790, Jun. 30, 2003.
Wattendorf, Uta, et al., "Phagocytosis of Poly(L-lysine)-graft-poly (ethylene glycol) Coated Microspheres by Antigen Presenting Cells: Impact of Grafting Ratio and Poly (ethylene glycol) Chain Length on Cellular Recognition," Biointerphases, vol. 1, No. 4, pp. 123-133, Dec. 2006.
Wilson, John T., et al., "Noncovalent Cell Surface Engineering With Cationic Graft Copolymers," Journal of the American Chemical Society, vol. 131, No. 51, pp. 18228-18229, Dec. 2009.
Winblade, Natalie Dawn, "Blocking Adhesion to Cell and Tissue Surfaces Via Steric Stabilization With Graft Copolymers Containing Poly(Ethylene Glycol) and Phenylboronic Acid," Dissertation (Ph. D.), California Institute of Technology, 182 pages, 2001.
Winblade, Natalie Dawn, "Sterically Blocking Adhesion of Cells to Biological Surfaces with a Surface-Active Copolymer Containing Poly(ethylene glycol) and Phenylboronic Acid," Journal of Biomedical Materials Research, vol. 59, No. 4, pp. 618-631, Mar. 2002.
Winterton, Lynn C., et al., "The Elution of Poly (Vinyl Alcohol) From a Contact Lens: The Realization of a Time Release Moisturizing Agent/Artificial Tear," Journal of Biomedical Materials Research, Part B, Applied Biomaterials, vol. 80, No. 2, pp. 424-432, Feb. 2007.
Authorized Officer Lee W. Young, International Search Report with Written Opinion International Application No. PCT/US 10/24585, 2 pages, dated Jun. 3, 2010.
European Patent Office, Munich, Supplementary European Search Report, Application EP 10 74 4296, 4 pages, dated Nov. 4, 2013.
"Aqueous Lubrication Inspired by Natural Mechanisms!"SuSoS AG, 1 page, Oct. 9, 2012 http://content.media.cebit.de.media/000095/0095798eng.pdf.
U.S. Appl. No. 14/327,846, filed Jul. 10, 2014, now U.S. Pat. No. 9,295,693.
U.S. Appl. No. 14/661,804, filed Mar. 18, 2015, now U.S. Pat. No. 9,283,248.
U.S. Appl. No. 15/085,072, filed Mar. 28, 2016.

* cited by examiner

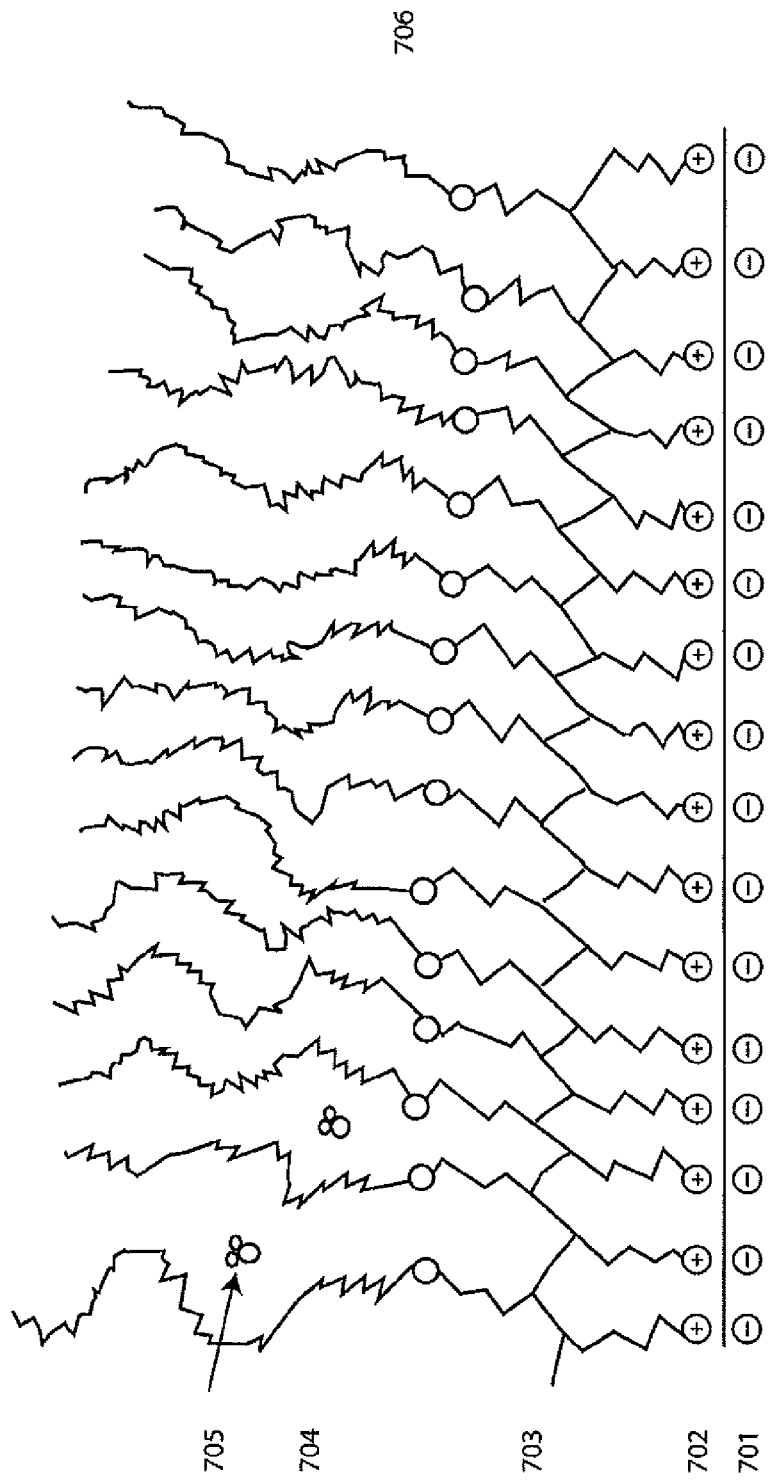

BI-FUNCTIONAL CO-POLYMER USE FOR OPHTHALMIC AND OTHER TOPICAL AND LOCAL APPLICATIONS

CROSS-REFERENCE TO RELATED APPLICATION

This application is a continuation of U.S. Ser. No. 14/661,804, filed Mar. 18, 2015, which is a continuation of U.S. Ser. No. 14/328,484, filed Jul. 10, 2014, now U.S. Pat. No. 9,005,596, which is a continuation of U.S. Ser. No. 12/708,329, filed Feb. 18, 2010, now U.S. Pat. No. 8,802,075, which claims the benefit of Provisional Application No. 61/153,416, filed on Feb. 18, 2009, the entire contents of which are incorporated herein by reference in their entirety.

FIELD OF THE INVENTION

The present invention provides topical and/or local delivery pharmaceutical formulations and coatings for extraocular devices, drug particles, or drug containing particles comprising a bi-functional polymer or co-polymer and methods for their use in modifying surface characteristics and/or changing the wettability of biological surfaces in a subject, or on the aforementioned devices. Formulations of the present invention are particularly useful in various applications including hydration, in particular treatment of dry eye syndrome and treatment of ophthalmic discomfort prevention of infection and/or adhesion of bacteria, viruses, proteins, toxins, and antigens and delivery of active pharmaceutical ingredients to biological surfaces. Formulations of the present invention can be used to alter the tribological properties of biological surfaces. Formulations of the present invention are also useful when combined with a host of topically delivered therapeutic agents. The formulations are also useful for coating extraocular devices, particularly contact lenses, to improve their biological compatibility.

BACKGROUND OF THE INVENTION

Poly(L-Lysine)-graft-poly(ethylene glycol)(PLL-g-PEG) is a water soluble copolymer consisting of a poly(L-Lysine) backbone and poly(ethylene glycol) side chains (Sawhney et al. Biomaterials 1992 13:863-870). The PLL chain, which carries multiple positive charges, spontaneously adsorbs onto negatively charged surfaces while PEG is a polynonion which serves as a non-binding domain. This adsorption is strong and occurs rapidly, and renders surfaces protein and cell resistant. Furthermore, PLL-g-PEG has been shown to improve the biocompatibility of materials. (Sawhney et al. Biomaterials 1992 13:863-870)

Various applications for the PLL-g-PEG graft co-polymer, block co-polymers, and dendrimers with similar binding characteristics have been described.

SUMMARY OF THE INVENTION

In one aspect, the invention provides a method for increasing the wettability of a biological surface or treating biological surface related discomfort in a subject, involving contacting the surface with a composition containing a copolymer having a positively charged, or hydrophobic or covalent bonding moiety and a hydrophilic moiety, where the contacting is effected in an amount and for a duration so as to increase the wettability or treat discomfort of the biological surface.

In one aspect, the invention provides a composition containing a copolymer having a positively charged, or hydrophobic, or covalent bonding moiety and a hydrophilic moiety and a pharmaceutically acceptable carrier.

In one aspect, the invention provides a pharmaceutical formulation containing an effective amount of a composition containing a copolymer having a positively charged, or hydrophobic, or covalent bonding moiety and a hydrophilic moiety and a pharmaceutically acceptable carrier.

In another aspect, the invention provides a method of storing a contact lens for at least 1 hour, involving providing the contact lens and a pharmaceutical formulation of the invention.

In one aspect, the invention provides a kit containing a contact lens and a pharmaceutical formulation of the invention, in a container that is unopened subsequent to manufacture.

In one aspect, the invention provides a kit containing a sterile pharmaceutical formulation of the invention and packaging materials therefore which permit use as an artificial tear product introducible into the eye.

In one aspect, the invention provides a kit comprising an extraocular device coated with the composition of the invention, and packaging materials therefore. In various embodiments, the packaging materials permit contacting of the extraocular device through the nozzle of an eye care solution container. In various embodiments, the extraocular device is an intracorneal inlay.

In one aspect, the invention provides a method for manufacture of a contact lens, involving providing a contact lens and contacting the contact lens with a composition of the invention.

In another aspect, the invention provides a kit containing a contact lens and a pharmaceutical formulation of the invention, in a container that is reusable.

In one aspect, the invention provides a copolymer coated nanoparticle, the surface of the nanoparticle containing a copolymer having a positively charged, or hydrophobic, or covalent bonding moiety and a hydrophilic moiety. In various embodiments, the nanoparticle further contains an active agent.

An aspect of the present invention relates to a method for changing wettability of and/or sterically modifying a biological surface in a subject comprising locally administering to the biological surface of the subject a pharmaceutical formulation comprising a bi-functional co-polymer. A copolymer composition can be contacted with an external body surface (e.g., skin) and/or used to prevent infection. Of particular interest and focus in this invention is the external surface of the eye including bulbar and palpebral conjunctiva and the cornea. Another aspect of the present invention relates to a method for treating dry eye syndrome comprising topically administering to an eye of a subject with dry eye syndrome a pharmaceutical formulation comprising a bi-functional co-polymer.

Another aspect of the present invention relates to a method for protecting a biological surface in a subject against pathogen or toxin attack, said method comprising topically or locally administering to the biological surface in the subject a pharmaceutical formulation comprising a bi-functional co-polymer.

Another aspect of the present invention relates to a method for delivering an active pharmaceutical ingredient to a biological surface in a subject comprising topically or locally administering to the biological surface of the subject a pharmaceutical formulation comprising a bi-functional co-polymer and the active pharmaceutical ingredient.

Another aspect of the present invention relates to a formulation for use in methods of changing wettability of (or otherwise sterically modifying or stabilizing) a biological surface in a subject, treating or preventing dry eye syndrome, treating or preventing discomfort related complications of LASIK surgery, treating or preventing infectious or inflammatory conditions of the external eye, protecting a biological surface in a subject against pathogens (bacteria, fungi, virus, prions, bioadhesive chemical agents) and/or delivering an active pharmaceutical ingredient to a biological surface in a subject, said formulation comprising a bi-functional co-polymer for topical and/or local administration to the subject.

Another aspect of the present invention relates to coating extraocular devices with a bi-functional co-polymer. Another aspect of the present invention relates to the use of the bi-functional co-polymers described herein to prevent or treat contact lens related discomfort and to reduce symptoms of contact lens intolerance.

Other aspects of the invention include the coating and thus protection of biological surfaces, such as the skin, especially mucous membranes inside the mouth, nose, throat, ear, vagina, for the purpose of maintaining hydration, and for protecting the biological surface from infection by pathogens and from toxins.

Other aspects of the invention include coating drug particles or particles containing drug to increase their utility by increasing half life and/or decreasing interaction with biologic phenomenon such as an immune response.

In various embodiments of any of the above aspects, the copolymer is a graft or a block copolymer. In various embodiments, the copolymer is a graft copolymer and contains a cationic backbone and side chains that are water soluble and non-ionic. In various embodiments, the copolymer is a graft copolymer and contains a water soluble non-ionic backbone and cationic side chains. In various embodiments, the copolymer is a block copolymer and contains at least one cationic block and at least one water soluble and non-ionic block. In various embodiments, the copolymer is a block copolymer and contains at least one block which is hydrophobic and at least one block which is water soluble and anionic. In various embodiments, the copolymer is a block copolymer and contains at least one block which is hydrophobic and at least one block which is water soluble and cationic. In various embodiments, the graft copolymer is PLL-g-PEG.

In various embodiments of any of the above aspects, the copolymer is a dendrimer. In various embodiments of any of the above aspects, the hydrophilic moiety is one of non-ionic or anionic. In various embodiments of any of the above aspects, the copolymer is a block copolymer and contains at least one block which is hydrophobic and at least one block which is water soluble and or non-ionic.

In various embodiments of any of the above aspects, the copolymer creates a covalent adhesion between the copolymer and the biological surface. In various embodiments of any of the above aspects, the contacted biological surface is the surface of an eye, a mucous membrane, or skin of a subject.

In various embodiments of any of the above aspects, the copolymer is 0.001 to 40% of the composition. In various embodiments of any of the above aspects, the copolymer is 0.001 to 25% of the composition.

In various embodiments of any of the above aspects, the composition further contains a second polymer. In various embodiments of any of the above aspects, the composition further contains a PLURONIC block copolymer. In various embodiments of any of the above aspects, the composition further contains one or more of a surfactant, a preservative, and a pharmaceutical ingredient including demulcents [Cellulose derivatives (Carboxymethylcellulose sodium, Hydroxyethyl cellulose, Hydroxypropyl methylcellulose, Methylcellulose), Dextran 70, Gelatin, Polyols (Glycerin, Polyethylene glycol 300, Polyethylene glycol 400, Polysorbate 80, Propylene glycol), Polyvinyl alcohol, Povidone] emollients (Lanolin, mineral oil, paraffin, petrolatum, white ointment, white petrolatum, white wax, yellow wax), sodium chloride, and vasoconstrictors (Ephedrine hydrochloride, Naphazoline hydrochloride, Phenylephrine hydrochloride, Tetrahydrozoline hydrochloride).

In various embodiments of any of the above aspects, the composition is contacted to the biological surface in an amount sufficient to change tribological properties of the biological surface of the subject. In various embodiments of any of the above aspects, the composition is contacted topically to an eye of a subject. In various embodiments of any of the above aspects, the composition is topically administered to an eye of a subject to treat dry eye, ophthalmic irritation, or corneal epithelial disease. In various embodiments, the composition is contacted to the eye by an eye drop or an eye care solution. In various embodiments, the method further involves administering to the eye of the subject a second, different eye drop. In various embodiments of any of the above aspects, the composition has a low viscosity artificial tear less than 20 cP, having prolonged tear film break up time. In various embodiments of any of the above aspects, the positively charged moiety is sufficient as a preservative in a topical ophthalmic formulation. In various embodiments of any of the above aspects, composition is in a volume sufficient for instillation in the eye, wherein the copolymer is PLL-g-PEG at a concentration of 0.1 to 3 wt %.

In various embodiments of any of the above aspects, the copolymer is immobilized on an extraocular device at the time of manufacture. In various embodiments, the copolymer is immobilized on the extraocular device covalently. In various embodiments, the immobilization is effected via an aldehyde plasma polymer interlayer and reductive amination. In various embodiments, the extraocular device is a contact lens.

BRIEF DESCRIPTION OF THE FIGURES

FIG. 7 is an example schematic drawing of the molecular behavior of the graft copolymer on an epithelial or ophthalmic device surface. This schematic demonstrates how the surface modifying polymer can be beneficial in altering the wettability or tribological properties of a surface and/or sterically modifying the surface so that the epithelium is protected and stays wet longer, or how an extra- or intra-ocular device may be made more biocompatible and less likely to foul with proteins and cellular debris. 701 represents the negatively charged epithelial surface (such as the cornea and conjunctiva) or negative charges on a device (such as a contact lens). 702 represents the positive charge on the NH3 terminal of lysine. 703 represents the anchoring poly (L) lysine backbone. 704 represents the flexible polyethylene glycol (PEG) side chains that form a brush. This brush can impart protein resistance, and is hydrated (705 is a water molecule), and thus there is also a change in wettability imparted onto the surface on which the graft (or block) copolymer electrostatically (or through hydrophobic interaction in some cases) adheres. 706 represents the entire graft copolymer molecule (PLL-g-PEG in this example). Steric stabilization is also imparted to exposed surfaces decreasing contact with proteins and cells, thereby protecting the epithelial or device surface from protein or cellular adhesion, inflammation or fouling. This figure is an example of PLL-g-PEG, but the same concept applies for other graft copolymers, generally, using either hydrophobic or cationic interaction with a surface combined with a hydrophilic moiety imparting the protective aspects of the invention herein described. Furthermore, the bi-functional co-polymers, block copolymers, and dendrimers may be diagrammed in a similar fashion, using a repeating moiety adherent to the surface and a repeating hydrophilic moiety imparting changes in wettability and protection. Furthermore, in some embodiments, the bi-functional copolymer may be covalently immobilized on the surface of a device such as a contact lens.

DETAILED DESCRIPTION OF THE INVENTION

Figure 1:
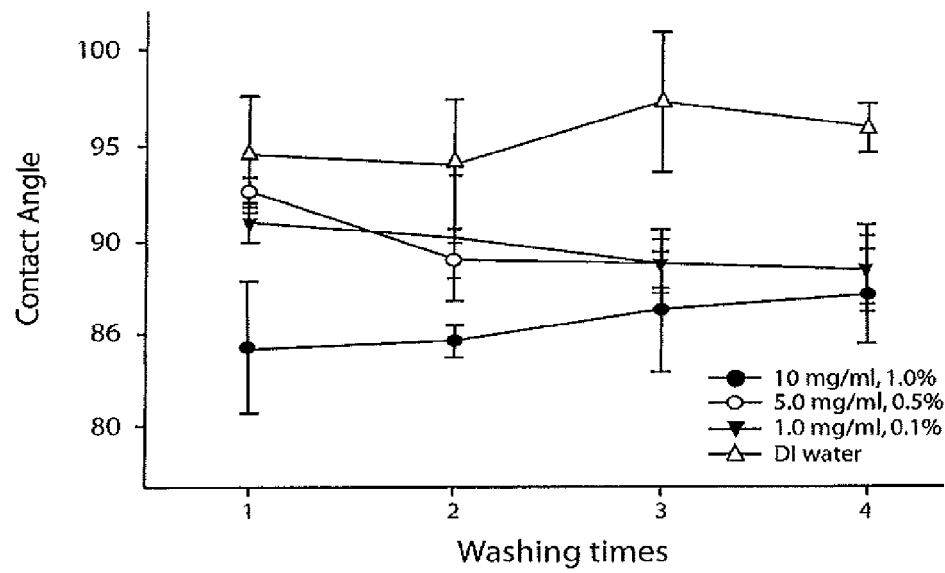
FIG. 1 shows results from an in vitro assessment of the ability of exemplary formulations of the present invention containing PLL-g-PEG to decrease contact angle of water to polystyrene. Formulations containing 10 mg/ml or 1% (closed circles), 5 mg/ml or 0.5% (open circles) or 1 mg/ml or 0.1% (closed triangles) were compared to a control of deionized water (open triangles).

It has now been found that topical or local administration of a formulation comprising a graft co-polymer having a positively charged or hydrophobic moiety and a hydrophilic moiety or a block co-polymer having a positively charged or hydrophobic moiety and a hydrophilic moiety to a biological surface alters and increases the wettability of certain surfaces, including a biological surface particularly the cornea conjunctiva and external surface of the eye, and does so for a prolonged period of time. A copolymer composition of the invention can be contacted with an external body surface (e.g., skin) and/or used to prevent infection.

By "moiety" it is meant the required portion of the polymer. For example, the moiety may be a monomer or one aspect of the polymer that imparts some characteristic required for activity and/or result. The PEG moiety imparts hydrophilicity. The PLL moiety imparts cationic charges. A phenylboronic moiety for example imparts an ability to form covalent attractions.

By "covalent" it is meant an interatomic bond characterised by the sharing of electrons. The bond can be reversible or permanent.

By "electrostatic" it is meant interaction between two molecules or two polymers or between a molecule or polymer and a biological or non-biological surface based on charge attractions—negative charge on one aspect of entity and positive charge on one aspect of the other.

By "bioadhesive" is meant a synthetic or natural polymer which binds to biological substrates such as mucosal membranes. Binding may be accomplished by electrostatic interaction, covalent attraction, hydrophobic interaction or other means.

By "hydrophobic interaction" it is meant an interaction between lipophilic moieties on polymers and surfaces to form adhesions or intermolecular aggregates or intramolecular interactions (particularly in aqueous based environments).

By "adhesive", it is meant tending to adhere, stick, or not come easily loose, or tending to persist.

By "increases the wettability" it is meant an increase in the relative degree with which an aqueous liquid will spread onto or coat a surface, including in the presence of other immiscible liquids. Increased wettability, according to the invention results in prolonged stability of the tear film keeping the cornea better coated by natural and artificial tear film components, reduce adhesion of inflammatory proteins, bacteria and inflammatory proteins to a biological surface or membrane of the subject.

Changes in wettability, however, are only part of the advantages conveyed by this invention. Surface modifications also include the steric stabilization of biological surfaces and extra-ocular ophthalmic device surfaces.

By "biological surface" is meant the surface of a bodily organ, whether it be exposed to the external environment, or internal to the body. For example, the surface of the eye includes the epithelial covered cornea and bulbar and palpebral conjunctiva, as well as the posterior tenons layer and sclera; the epithelial layers of the gastrointestinal tract or the skin are included, membranes such as mucous membranes, including oral, nasal, respiratory, urinary tract including the bladder, and vaginal mucous membranes. Other surfaces include the capsules of organs such as the spleen and liver, and the outermost aspect of bone, cartilage, and muscle, as well as wounds and areas where there is unprotected sub-epithelial biological tissue exposure.

By "tribological properties" it is meant properties of interaction of surfaces in relative motion. For example, a contact lens on the surface of the eye with some movement on the corneal surface and/or with the act of blinking whereby the palpebral conjunctival surface moves over the contact lens constitutes a state of relative motion between two surfaces. Likewise, blinking whereby the palpebral conjunctival surface moves over the cornea and bulbar conjunctiva constitutes a state of relative motion between two surfaces. Tribological properties can include but are not limited to properties such as lubrication, friction, and wear.

By "subject", as used herein it is meant to be inclusive of all animals and in particular mammals such as, but not limited to, humans and dogs as well as agricultural animals such as bovine, ovine, and porcine.

By "prolonged period of time" means that the formulation has an effect that lasts longer than leading artificial tear products on the market, which has been shown to be at least two hours with the sample formulation, but "prolonged period of time" can also mean longer than 20 minutes, as most ophthalmic topical products are washed out of the eye in 20 minutes. A "prolonged" period of time includes 30, 45, 50 minutes, as well as 1, 2, 5, 10, 24 hours, or 1, 2, 5, 10 or 30 days or more.

By "steric stabilization" or "steric modification" means that the surface effects of the graft and block co-polymers results in a hydrophilic moiety projected away from the biological surface, drug particle or drug containing particle that imparts characteristics such as low protein adsorption and cell adhesion. Such an effect can also be called steric repulsion and surface exclusion effects secondary to the PEG moieties (termed "brushes" in some descriptions) on the graft copolymers. Other hydrophilic chains can accomplish the same purpose in some embodiments. High surface water retaining capacities, osmotic repulsion, and charge neutrality may also contribute to this "steric stabilization" effect.

By "storage" is meant time on the shelf in a container, and storage time includes 1, 2, 5, 10, 30, 180, or 360 days or more.

Accordingly, the present invention provides methods for changing wettability of (or sterically stabilizing or otherwise modifying) biological surfaces or membranes in a subject via topical or local administration of a pharmaceutical formulation comprising a graft co-polymer having a positively charged or hydrophobic moiety and a hydrophilic moiety or a block co-polymer having a positively charged or hydrophobic moiety and a hydrophilic moiety to a biological surface of a subject, or both. Pharmaceutical formulations can be administered topically or locally in accordance with methods of the present invention to biological surfaces of a subject including, but not limited to, skin, mucous membranes, hair, and the surface of the eye.

According to the present invention, through the use of the block and graft co-polymers described herein, certain drugs and active biopharmaceutical agents will have improved efficacy and decreased frequency of dosing needs as formulations using the block or graft copolymers can bring such active pharmaceutical agents into contact with epithelial surfaces, such as the cornea and conjunctiva, for prolonged periods of time.

According to the present invention, through the use of the block and graft co-polymers described herein, the tolerability of extraocular devices such as contact lenses, shunts, retinal implant/explant materials and devices for scleral buckles, and drug delivery devices, can be improved. Furthermore, ophthalmic sutures may be coated with these polymers decreasing tissue reaction and reducing unwanted particle or bacterial adherence. First, the devices can be coated (using electrostatic or hydrophobic interactions or through covalent immobilization), with the said polymers increasing wettability, modifying surface characteristics, and/or sterically stabilizing and decreasing the adherence of unwanted antigens, cells, proteins, and other particles to them. Second, by protecting the epithelial surface or other ophthalmic tissues (through turnover and/or exchange of these adherent polymers with a biological surface and/or through the separation of the device from the epithelial surface by the "brush" characteristics of the hydrophilic moieties), the devices may be more tolerable.

By "extraocular device" is meant medical devices that do touch but do not reside entirely inside the eye. A contact lens is an extraocular device. An intra-corneal inlay is an extraocular device because it does not breach the intraocular environment. A glaucoma shunt, is an extraocular device because the vast majority of the device (except for the distal tip of the tube) resides outside the eye. A scleral buckle is an extraocular device.

By "co-polymers" is meant a polymer with two or more different monomers. Block, graft, and dendrimer co-polymers are the major, but not only types of co-polymers referenced herein.

By "bi-functional" is meant the co-polymer has two or more different functions that derive from the different moieties or monomers inherent to the co-polymer. For example a hydrophilic moiety or monomer has the property of wettability and a cationic backbone has the property of bioadhesiveness. Joined together in a co-polymer both functions remain. Specifically, bifunctional co-polymers relates to but is not limited to graft, block, a and dendrimer co-polymers. Critical to this invention is the novel use of bi-functional graft copolymers in ophthalmic use.

By "ophthalmic use" is meant used on or in or adjacent to the eye. Topical eye drops are included in ophthalmic use as is subconjunctival, peribulbar and eyelid use. Use on contact lenses and extraocular devices is included in ophthalmic use.

By "pluronic" is meant poloxamers or trade name pluronic copolymers that are composed of nonionic triblock copolymers composed of a central hydrophobic chain of polyoxypropylene (poly(propylene oxide)) flanked by two hydrophilic chains of polyoxyethylene (poly(ethylene oxide))

By "preserved" it is meant there is a substance or preparation added to a product to destroy or inhibit the multiplication of microorganisms.

According to the present invention, through the use of the block and graft co-polymers described herein, the tolerability of extraocular devices (such as contact lenses and intracorneal optical devices), can be improved. First, the devices can be coated with the said polymers increasing wettability and decreasing the adherence of unwanted antigens, cells, proteins, and other particles to them. Second, by protecting the adjacent tissue structures, the devices may be more tolerable and function better i.e. through less protein or cellular interaction on the device. In the case of intracorneal inlay technology, such a coating may improve the clinical performance of such devices in multiple ways.

Graft co-polymers used in the methods and formulations of the present invention are polymers having a linear section of repeat units called the "backbone", with at least one side chain of repeat units (called a graft), usually of a different chemistry, branching from a point along the backbone. In one embodiment, the graft co-polymer comprises a cationic backbone and side chains that are water soluble and nonionic. In another embodiment, the graft copolymer comprises a water soluble non-ionic backbone and cationic side chains.

Block co-polymers used in the methods and formulations of the present invention are polymers in which linear sections of a first section of repeat units are connected end-to-end with linear sections of subsequent repeat units that are chemically dissimilar to the first.

Dendrimers comprised of cationic and hydrophilic polymeric moieties can similarly be used as identified above in the methods and formulations of the present invention to accomplish similar structural and steric alterations of the biological surface (particularly the eye), drug particles or drug containing particles.

By "dendrimers" it is meant co-polymer molecules that are repeatedly branched.

Also included in the invention is the use of graft, block, and dendrimeric copolymers with multi-functionality in topical applications and formulations including ophthalmic applications and formulations. For example, a polymer where there is a moiety bonded to one constituent polymer that promotes covalent bond formation between the copolymer and biological surfaces such as the surface of the eye or between the copolymer and extraocular devices that also project a comb or a brush type of hydrophilic moiety, is claimed. As can be seen to one skilled in the art, the results accomplished with the use of electrostatic interaction between the polymer and biological surfaces and the external environment or extraocular devices can be accomplished using similarly designed bi- and multi-functional polymers that promote the formation of a covalent bond instead of or in addition to electrostatic attraction only. For example, the use of phenylboronic acid (PBA) or other boron based moieties in the polymer backbone provide a method for the formation of covalent complexes between copolymers and biological surfaces and between copolymers and extraocular devices. Even though not called out continuously throughout this document, the method of using covalent, electrostatic and hydrophobic attraction (or any combination or either) in ophthalmic applications is described. PLL-g=(PEG;PBA) is an example of a polymeric structure that would impart the described characteristics.

Formulations for use in the methods of the present invention comprise a block or graft co-polymer having one section, either the backbone, the graft or the block, that adheres to a biological surface tissue such as, but not limited to, the eye surface by electrostatic or hydrophobic forces (or covalent), and another, chemically different section, either the backbone, the graft, or block, that is hydrophilic and retains moisture (sometimes called a "brush" or a "PEG brush" in some embodiments), or allows an aqueous film to readily spread over and thus wet the biological surface. Sometimes the graft copolymers such as PLL-g-PEG, for example, can be referred to as comb co-polymers. Furthermore, the "brush" that is composed of water soluble polymers that are biocompatible can in aqueous environment, provide oil free lubricity (Drobeck et al. Langmuir. 24(4): 1484-8).

The surface modifications imparted by graft and block co-polymers herein described may include, but are not limited to changes in wettability, steric modification or steric stabilization, steric repulsion, surface exclusion effects, high surface water retaining characteristics, charge neutrality, and osmotic repulsion. These and other effects on the surfaces are important processes that may convey clinically meaningful benefits to subjects and to the performance of medical devices. The tissue-adhesive sections of a bi-functional co-polymer in the formulations used in the methods of the present invention may be cationic, in which case the polymer adheres to the biological surface by electrostatic attraction, or may be hydrophobic in which case the polymer adheres to the biological surface by hydrophobic interaction, or may involve a covalent complex. In some cases, the wettability of the biological surface may result in whole or in part from modification of a liquid layer adjacent the surface, such as the mucous layer adjacent the cornea. In some cases the tissue surface modification may simply impart a lubricious protective coating over ophthalmic tissue or extraocular devices. It may also alter the tribological properties of tissues and extraocular devices.

Aspects of the invention include copolymer coated nanoparticles which can encompass active agents, including drugs (small molecule, chemical, pharmaceutical, biologic) or allergens (viruses, bacteria, yeast, prions). The nanoparticles have exposed on their surface (i.e., are coated with) a copolymer, where the copolymer has a positively charged, or hydrophobic, or covalent bonding moiety and a hydrophilic moiety. Nanoparticles are not of sufficient size to encompass cells. Nanoparticles are not microspheres. Other aspects of the invention include coating drug particles or particles containing drug to increase their utility by increasing half life and/or decreasing interaction with biologic phenomenon such as an immune response. For intramuscular injection, the nanoparticle size should be 1 mm or smaller diameter; for inhalation, the nanoparticle size should be 10 microns or smaller in diameter; for IV injection, the nanoparticle size should be 1 micron or smaller in diameter.

Aspects of the invention include copolymer coated nanoparticles which can encompass active agents, including drugs (small molecule, chemical, pharmaceutical, biologic) or allergens (viruses, bacteria, yeast, prions). The nanoparticles have exposed on their surface (i.e., are coated with) a copolymer, where the copolymer has a positively charged, or hydrophobic, or covalent bonding moiety and a hydrophilic moiety. Nanoparticles are not of sufficient size to encompass cells. Nanoparticles are not microspheres. Other aspects of the invention include coating drug particles or particles containing drug to increase their utility by increasing half life and/or decreasing interaction with biologic phenomenon such as an immune response.

Nanoparticles of the invention have an effective average particle size of less than about 1000 nm (i.e., 1 micron), less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. By "an effective average particle size of less than about 2000 nm" it is meant that at least 50% by weight of the active agent particles have a particle size less than the effective average, i.e., less than about 2000 nm, 1900 nm, 1800 nm, etc., when measured by the above-noted techniques. In other embodiments of the invention, at least about 70%, at least about 90%, or at least about 95% of the active agent particles have a particle size less than the effective average, i.e., less than about 2000 nm, 1900 nm, 1800 nm, etc. For intramuscular injection, the nanoparticle size should be 1 mm or smaller diameter; for inhalation, the nanoparticle size should be 10 microns or smaller in diameter; for IV injection, the nanoparticle size should be 1 micron or smaller in diameter.

Nanoparticles of the invention can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are herein incorporated by reference.

The resultant nanoparticulate active agent compositions can be utilized in solid or liquid dosage formulations, such as controlled release formulations, solid dose fast melt formulations, aerosol formulations, nasal formulations, lyophilized formulations, tablets, capsules, solid lozenge, powders, creams, ointments, etc.

The nanoparticles of the invention can be contacted with a copolymer having a positively charged, or hydrophobic or covalent bonding moiety and a hydrophilic moiety after attrition. One or more secondary surface stabilizers may also be added before or after attrition. The active agent particles can be reduced in size in the presence of a copolymer having a positively charged, or hydrophobic or covalent bonding moiety and a hydrophilic moiety. Other compounds, such as a diluent, can be added to the copolymer active agent/surface stabilizer composition during the size reduction process (e.g., milling). Dispersions can be manufactured continuously or in a batch mode.

Another method of forming the copolymer coated nanoparticles of the invention is by microprecipitation. This is a method of preparing stable dispersions of copolymers or active agents in the presence of one or more surface stabilizers and one or more colloid stability enhancing surface active agents free of any trace toxic solvents or solubilized heavy metal impurities. Such a method comprises, for example: (1) dissolving the copolymer or active agent in a suitable solvent; (2) adding the formulation from step (1) to a solution containing a copolymer having a positively charged, or hydrophobic or covalent bonding moiety and a hydrophilic moiety and/or active agent and optionally one or more secondary surface stabilizers, to form a clear solution; and (3) precipitating the formulation from step (2) using an appropriate non-solvent. The method can be followed by removal of any formed salt, if present, by dialysis or diafiltration and concentration of the dispersion by conventional means.

Exemplary homogenization methods of preparing copolymer coated nanoparticles are described in U.S. Pat. No. 5,510,118, for "Process of Preparing Therapeutic Compositions Containing Nanoparticles." Such a method comprises dispersing nanoparticles in a liquid dispersion medium in which the copolymer or active agent is soluble, followed by subjecting the dispersion to homogenization to reduce the particle size of the active agent to the desired effective average particle size. The nanoparticles can be reduced in size in the presence of a copolymer having a positively charged, or hydrophobic or covalent bonding moiety and a hydrophilic moiety and/or active agent, and, if desired, one or more additional surface stabilizers. Alternatively, the nanoparticles can be contacted with the copolymer and/or active agent and, if desired, one or more additional surface stabilizers either before or after attrition. Other compounds, such as a diluent, can be added to the active agent/copolymer composition either before, during, or after the size reduction process. Dispersions can be manufactured continuously or in a batch mode.

The copolymer coated nanoparticles of the invention may contain an active agent. The active agent may be contained within the nanoparticle, on the surface of the nanoparticle, in the copolymer coating of the nanoparticle, or on the surface of the copolymer coating of the nanoparticle. Active agents that can be used with the copolymer coated nanoparticle include without limitation drugs (small molecule, chemical, pharmaceutical, biologic) or allergens (viruses, bacteria, yeast, prions). Active agents may be therapeutic, or diagnostic agent. A therapeutic agent can be a pharmaceutical agent, including biologics such as proteins, peptides, and nucleotides, or a diagnostic agent, such as a contrast agent, including x-ray contrast agents. The active agent exists either as a discrete, crystalline phase, an amorphous phase, a semi-amorphous phase, a semi-crystalline phase, or mixtures thereof. The crystalline phase differs from a non-crystalline or amorphous phase which results from precipitation techniques, such as those described in EP Pat. No. 275,796. Two or more active agents can be used in combination.

The active agent can be selected from a variety of known classes of drugs, including, for example, proteins, peptides, nucleotides, anti-obesity drugs, nutraceuticals, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

Active agents to be administered in an aerosol formulation are preferably selected from the group consisting of proteins, peptide, bronchodilators, corticosteroids, elastase inhibitors, analgesics, anti-fungals, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, respiratory illness therapies associated with acquired immune deficiency syndrome, an oncology drug, an anti-emetic, an analgesic, and a cardiovascular agent.

A description of these classes of active agents and a listing of species within each class can be found in Martindale, *The Extra Pharmacopoeia*, Twenty-ninth Edition (The Pharmaceutical Press, London, 1989), specifically incorporated by reference. The active agents are commercially available and/or can be prepared by techniques known in the art.

Exemplary active agents to be applied to mucous include dental applications, such as oral bioadhesive nanoparticulate lidocain formulations, bioadhesive nanoparticulate fluoride treatments, application to the lungs, throat, GIT, application to wounds, etc. Also included is application to the throat using a liquid containing a bioadhesive nanoparticulate formulation containing, for example, menthol or other numbing compound for treatment of coughs or sore throats. The stomach and GIT can also be treated using bioadhesive formulations. This is particularly useful for treatment of diseases associated with the mucous of the gastrointestinal tract, such as Crohn's Disease. Other pharmaceutical therapeutic methodologies include oral dosing, nasal administration, vaginal administration, ocular administration, colonic, and subcutaneous administration.

The compositions of the invention also encompass food products. For example, spice, oleoresin, flavor oil, color, or chemicals are often added during food processing to produce the desirable flavors, taste, and appearance. These agents can be included in a bioadhesive nanoparticulate composition of the present invention for increased adhesion to biological surfaces. Bioadhesive nanoparticulate flavoring agents could be used in products such as gums to produce prolonged flavor.

Other exemplary uses of the novel bioadhesive formulations are provided: teeth can be treated with teeth whiteners or fluoride bioadhesive compositions; bones can be treated with calcium bioadhesive compositions; nails can be treated with color or strengthening bioadhesive formulations; insects or pests can be treated with insecticides or other toxic compositions to the pest. In sum, the compositions are useful in treating any biological surface, or a surface derived from a biological material. Feathers and scales of animals can be treated, as well as other animal biological surfaces such as chitin.

For the purpose of this invention, the description that follows below on the different types of graft and block co-polymers applies to invention embodiments of formulations for ophthalmic and medical topical and pharmaceutical use, and to the use of these graft and block co-polymers in the setting of extra- and intra-corneal ophthalmic devices as coatings, and for ways of treating, storing, or manufacturing, or reapplying the coatings to these devices:

Examples of cationic polymer sections of graft or block co-polymers of formulations useful in the methods of the present invention include, but are not limited to: polyp lysine) (PLL), polylysine [including poly-D-lysine (PDL), poly-DL-lysine, poly-e-CBZ-D-lysine, poly-e-CBZ-DL-lysine, or poly-e-CBZ-L-lysine) polyornithine (i.e., poly-DL-ornithine, poly-L-ornithine or poly-S-CBZ-DL-ornithine), and the like)], [note Pub. No.: WO/1993/018649 International Application No.: PCT/US1993/002609 contains additional descriptions of polycatioinc water soluble graft copolymers and is incorporated here by reference], poly(2-vinyl pyridine, poly(4-vinyl pyridine) and vinyl co-polymers containing those repeat units, and poly(aminoethyl methacrylate) homo- and co-polymers containing N,N dimethylaminoethylmethacrylate) repeat units. In general, polymers containing acrylates and acrylalmides can serve as cationic sections of the bi-functional co-polymers. Additional exemplary cationic polymers include, but are not limited to, poly(trimethylammonioethyl methacrylate chloride), poly-(2-(dimethylamino) ethyl methacrylate) (pDMAEMA), poly-(2-(dimethylamino) ethyl methacrylateco-methacrylic acid) (pDMAEMA-co-MAA) and poly-(2-methyl-acrylic acid 2-[(2-dimethylamino-ethyl)-methylamino]-ethyl ester) (pDAMA), and cation guar gum. Another cationic polymer section which can be used is chitosan (a co-polymer of glucosamine and N-acetyl glucosamine where 5-100% of the repeat units are glucosamine) and synthetic derivatives thereof. The use of amines and other positively charged amino acids bound to polymeric configurations to mimic the cationic polymeric activities so described. In general, molecular structures that can impart a positive external charge on a block or graft copolymer or a dendrimer are included in the invention.

Examples of hydrophobic polymer sections of bi-functional co-polymers of formulations useful in the methods of the present invention include, but are not limited to, long-chain aliphatic hydrocarbons, polyethylene, poly(propylene oxide), polystyrene, poly(methylmethacrylate), poly(butylenes oxide), and the like. In general, molecular structures that can impart an exposed hydrophobic domain on a block or graft copolymer are included in the invention.

The hydrophilic section of the polymer may be non-ionic if the tissue adhering section is cationic, or non ionic or anionic if the tissue-adhering section is non-ionic (and hydrophobic). Examples of non-ionic hydrophilic polymer sections of formulations useful in methods of the present invention include, but are not limited to, poly(ethylenegly-col) (PEG), poly(vinylalcohol), poly(vinylpyrrolidinone), dextrans and the like. Examples of anionic hydrophilic polymer sections include homopolymers and co-polymers containing, for example, acrylic acid, methacrylic acid, itaconic acid, maleic acid, styrene sulfonic acid, carboxymethylcellulose, carboxyethylcellulose, succinylated chitosan, cellulose sulfate, and the like. Additional exemplary hydrophilic polymers include, but are not limited to, poly (dimethylamino)ethyl methacrylate and poly hydroxypropyl methacrylate (PHPMA).

The adsorbing segment could also comprise a boronate group selected from the group consisting of phenylboronic acid (PBA), 2-carboxyethaneboronic acid, 1,2-dicarboxyethaneboronic acid, .beta.,.beta.'-dicarboxyethaneboronate, .beta.,.gamma.-dicarboxypropaneboronate, 2-nitro- and 4-nitro-3-succinamidobenzene boronic acids, 3-nitro-4-(6-aminohexylamido)phenyl boronic acid, {4-[(hexamethyl-enetetramine)methyl]phenyl}boronic acid, 4-(N-methyl) carboxamidobenzene boronic acid, 2-{[(4-boronphenyl) methyl]-ethylammonio}ethyl and 2-{[(4-boronphenyl) methyl]diethylammonio}-ethyl groups, succinyl-3-aminophenylboronic add, 6-aminocaproyl-3- aminophenylboronic acid, 3-(N-succinimidoxycarbonyl) aminophenylboronate, p-(.omega.-aminoethyl) phenylboronate, p-vinylbenzeneboronate, N-(3-dihydroxyborylphenyl)succinamic acid, N-(4-nitro-3-dihydroxyborylphenyl)succinamic acid, O-dimethylaminomethylbenzeneboronic acid, 4-carboxybenzeneboronic acid, 4-(N-octyl)carboxamidobenzeneboronic acid, 3-nitro-4-carboxybenzeneboronic acid, 2-nitro-4-carboxybenzeneboronic acid, 4-bromophenylboronate, p-vinylbenzene boronate, 4-(.omega.-aminoethyl)phenylboronate, catechol [2-(diethylamino)carbonyl, 4-bromomethyl]phenyl boronate, and 5-vinyl-2-dimethylaminomethylbenzeneboronic acid.

Adhesion resistant segments is another way to describe an important component of the copolymer. Adhesion resistant moieties could include: polyalkylene oxides, mixed polyalkylene oxides, polysaccharides, polyvinyl alcohol, poly-N-vinyl pyrrolidone, noncationic polyacrylates, noncationic polymethacrylates, and mixtures and copolymers of these constituents.

In general, the chains and block and graft copolymer moieties may be any length, size, or molecular weight, and may have any number of repeat rates of the polymer components. Imparting beneficial properties is the main variable that will determine specific size, weights, chain lengths, and repeat specifications for applications described herein. As an example, PEG of different molecular weights can be grafted onto the poly-(L-lysine) at different ratios of PLL:PEG, to optimize the polymer architecture for wettability, steric stabilization, and protein resistance. Additionally, other factors, such as cost, process development requirements, manufacturing, and biologic tolerability will go into making specific size, weight, chain length, and repeat characteristic specification decisions. For these polymers, polydispersity may be acceptable over both wide and narrow ranges, and product specifications will be made based on this characteristic as well. However, this invention claims the use of all sizes, weights, chain lengths, and repeat characteristics of these graft and block co-polymers for uses and methods described herein.

Graft co-polymers may have a cationic (or non-ionic hydrophobic) backbone made from a polymer chosen from the list, supra, and hydrophilic grafts, or have a hydrophilic backbone, and cationic (or non-ionic hydrophobic) grafts chosen from the list, supra. For graft co-polymers, grafts may arise from every repeat unit in the backbone or may be intermittently spaced along the backbone (with uniform or random frequency). For example, a useful polymer in formulations for use in the methods of the present invention is PLL-g-PEG where the backbone is the cationic polymer poly(L-lysine) and the grafts are made from the hydrophilic polymer poly(ethylene glycol). The PLL backbone may be from 3 repeat units to several thousand repeat units long, and the PEG grafts may be from 1 to several thousand repeat units long. The PEG grafts may be attached to every PLL repeat unit, every other PLL repeat unit, every third repeat unit or less frequent. In one embodiment, there is a PEG graft on average at every third PLL repeat unit. Regarding PLL, the PLL chain length can be any length, and made from PLL derived from fermentation processes or synthetic polymerization reactions. The molecular weight of the PLL backbone can be in the range of several thousand Daltons (3,000 to 5,000) to tens of thousands of Daltons 15,000 to 30,000, or higher. The chain length can be as short as ten lysine groups or as long as one to two hundred (or longer) lysine groups. The polyamino acid chain bonds may be epsilon or alpha based. By block or graft co-polymers it is meant to describe the architecture of the polymer.

An additional exemplary polymer for use in formulations used in the methods of the present invention is PLL-g-dextran. Similar detailed analysis and variability descriptions (as in the paragraph above) can be made for PLL-g-dextran, and for many other graft co-polymers claimed in this invention. Those skilled in the art will identify methods to mimic the behavior of the copolymers herein described using different monomers and moieties, and those methods and compositions are claimed.

Block co-polymers or dendrimers comprising at least one block or moiety that is cationic and at least one block or moiety that is water soluble and non-ionic are also useful in formulations for use in methods of the present invention. In one embodiment, the co-polymer comprises at least one block which is hydrophobic and at least one block which is water soluble and anionic, cationic or non-ionic.

Examples of water soluble non-ionic co-polymer blocks or moieties include, but are not limited to, poly(ethylene glycol) (PEG), polyvinyl alcohol (PVA), poly(hydroxyethyl methacrylate) (pHEMA), poly(acrylamide), poly (vinyl pyrrolidone) (PVP), poly(ethyl oxazoline) (PEOX), polysaccharides, and copolymers of any two or more thereof.

Examples of water soluble anionic co-polymer blocks or moieties include, but are not limited to, polyacrylic acid (PAA), polymethacrylic acid, poly(sodium styrene sulfonate), carboxylated cellulosics such as carboxymethylcellulose (CMC), poly(itaconic acid), poly(maleic acid), poly (acrylamidopropanesulfonic acid), anionic natural gums, anionic carbohydrates, carageenan, alginates and hyaluronic acid.

Examples of water soluble cationic co-polymer blocks include, but are not limited to, polymers based on vinyl pyridine, N,N-dimethylaminoethylacrylate, N,N-dimethylaminoethylmethacrylate, other acrylate and acryamide polymeric structures, allyl tri(alkyl) ammonium halides, poly (amino styrene), certain types of cation guar gums, chitosan, polyethyleneimine, polyallylamine, polyetheramine, polyvinylpyridine, polysaccharides having a positively charged functionality thereon, polyamino acids such as, but not limited to, poly-L-histidine, poly-im-benzyl-L-histidine, poly-D-lysine, poly-DL-lysine, poly-L-lysine, poly-$\epsilon$-CBZ-D-lysine, poly-$\epsilon$-CBZ-DL-lysine, poly-$\epsilon$-CBZ-L-lysine, poly-DL-ornithine, poly-L-ornithine, poly-$\Delta$-CBZ-DL-ornithine, poly-L-arginine, poly-DL-alanine-poly-L-lysine, poly (-L-histidine, L-glutamic acid)-poly-DL-alanine-poly-L-lysine, poly(L-phenylalanine, L-glutamic acid)-poly-DL-alanine-poly-L-lysine, and poly(L-tyrosine, L-glutamic acid)-poly-DL-alanine-poly-L-lysine, copolymers of L-arginine with tryptophan, tyrosine, or serine, copolymers of D-glutamic acid with D-lysine, copolymers of L-glutamic acid with lysine, ornithine, or mixtures of lysine and ornithine, and poly (L-glutamic acid), and the use of amines and other positively charged amino acids bound to polymeric configurations to mimic the cationic polymeric activities so described.

Examples of hydrophobic co-polymer blocks include, but are not limited to, alkanes, alkenes, alkynes, poly(isobutylene), polyesters such as poly(caprolactone) (PCL), poly (lactic acid) (PLA), poly(glycolic acid) (PGA), and copolymers therefrom (PLGA), polyamides such as nylon(6,6) and Nylon(12), polyurethanes, poly(propylene oxide), poly(tetramethylene oxide), polyethylene, polypropylene, polystyrene, poly(acrylates) such as polymethyl acrylate (PMA), poly(methacrylates) such as poly(methylmethacrylate)

(PMMA), poly(sulfones), poly(etheretherketones) (PEEKs), poly(phosphazines), poly(carbonates), poly(acetals) and poly(siloxanes).

As described supra, a host of additional adsorbing agents can be utilized in the polymer construction.

As will be understood by the skilled artisan upon reading this disclosure, triblock configurations can be used. An exemplary block co-polymer comprising a triblock configuration is PLURONIC® F127, also referred to as Poloxamer 407, containing a poly(ethylene oxide) hydrophilic block ("PEO"), a poly(propylene oxide) hydrophobic block ("PPO") and another PEO block. Other block co-polymers for use in the present invention may contain only one hydrophilic block and one hydrophobic block, or may contain several alternating blocks, for example the PPO-PEO-PPO block co-polymers (PLURONIC®, block co-polymers based on ethylene oxide and propylene oxide, BASF, Florham Park, N.J.). Additional exemplary PLURONIC block co-polymers useful in the present invention include, but are not limited to, PLURONIC 10R5, PLURONIC 17R2, PLURONIC 17R4, PLURONIC 25R2, PLURONIC 25R4, PLURONIC 31R1, PLURONIC F 108 Cast Solid Surfacta, PLURONIC F 108 Pastille, PLURONIC F 108 Prill, PLURONIC F 108NF Prill Polaxamer 338, PLURONIC F 127 Prill, PLURONIC F 127 NF, PLURONIC F 127 NF 500 BHT Prill, PLURONIC F 127 NF Prill Poloxamer 407, PLURONIC F 38, PLURONIC F 38 Pastille, PLURONIC F 68, PLURONIC F 68 Pastille, PLURONIC F 68 LF Pastille, PLURONIC F 68 NF Prill Poloxamer 188, PLURONIC F 68 Prill, PLURONIC F 77, PLURONIC F 77 Micropastille, PLURONIC F 87, PLURONIC F 87 NF Prill Poloxamer 237, PLURONIC F 87 Prill, PLURONIC F 88 Pastille, PLURONIC F 88 Prill, PLURONIC F 98, PLURONIC F 98 Prill, PLURONIC L 10, PLURONIC L 101, PLURONIC L 121, PLURONIC L 31, PLURONIC L 35, PLURONIC L 43, PLURONIC L 44, PLURONIC L 44 NF Polaxomer 124, PLURONIC L 61, PLURONIC L 62, PLURONIC L 62 LF, PLURONIC L 62D, PLURONIC L 64, PLURONIC L 81, PLURONIC L 92, PLURONIC L44 NF INH surfactant Polaxamer 124, PLURONIC N 3, PLURONIC P 103, PLURONIC P 104, PLURONIC P 105, PLURONIC P 123 Surfactant, PLURONIC P 65, PLURONIC P 84, and PLURONIC P85. Where applicable, all particle sizes of the block co-polymers are included, for example PLURONIC F127 and PLURONIC F87 are available as prill and micro-prill products. Non-ionic surfactants, for example, containing a hydrophobic segment and a PEO block are considered here as block co-polymers. The use of these commercially available agents specifically in combination in formulations with bifunctional copolymers here described including cationic and other adsorbing moieties coupled with hydrophilic or non reactive elements is identified.

Additional exemplary block or graft co-polymers or dendrimers which can be used in the present invention are disclosed in U.S. Pat. No. 5,578,442 and U.S. Pat. No. 5,834,556, as well as U.S. Pat. Nos. 462,990; 5,627,233; 5,567,440; 5,849,839; 5,820,882; 5,380,536; 5,232,984; 6,231,892; 6,743,521; 7,316,845; 2,286,590; 6,596,267; 7,029,688; 6,350,527; 6,652,902. Teachings of each of which are herein incorporated by reference in their entirety.

By "formulations" it is meant the particular mixture of base chemicals and additives required for a product.

As mentioned previously, the examples of multi-functional or bifunctional copolymers described above can be used in formulations for topical ophthalmic use and for coating extraocular and intra-corneal devices. However, the invention is not limited only to those entities described above, other variations or types of graft and block co-polymers having properties described herein is an embodiment of the invention. The invention is not limited only to those block and graft co-polymers named and described in detail herein.

The block or graft co-polymers are included in formulations for use in the methods of the present invention at weight percent concentrations ranging between 0.001% and 40%, more typically 0.01% to 25%, of the formulation. An effective amount is claimed. In the Examples in which the formulation is described at present, the amounts of co-polymers are between about 0.1% and 2%. In addition the amount of bi-functional co-polymer can fall within other smaller ranges e.g., 0.01% to 3%, 0.1% to 2.5%, or 0.5 to 2%.

The combinations of different copolymers can be that each is (weight/weight) between 0.01% and 2% but can have ranges high as wide as 0.01% and 5%.

An effective amount is an amount that increases the wettability of a given biological surface, or contact lens surface; or that changes or modifies the surface in a favorable way; such modification can include but is not limited to steric stabilization, steric repulsion, high surface water retaining capacity, charge neutrality, surface exclusion effects, or osmotic repulsion. The extent of increase in wettability will vary with the application and with the disease or disease symptom that is being treated or prevented. An effective amount is an amount that leads to beneficial biological surface modification characteristics, as described above.

The bi-functional copolymers are used in any of these concentrations to impart favorable characteristics to a product for use in humans or other mammals either with or without an active pharmaceutical ingredient. An active pharmaceutical ingredient can be added to these formulations and the active agent will be used in weight percent concentrations from between 0.0001% to 40%, more typically from 0.01% to 10%. The copolymers can be used with a preservatives such as, but are not limited to, Polixetonium, polyquaternium-42, Polyquaternium-1, Polyquat, Alkyl-hydroxy benzoate preservatives, parabens, hydrogen peroxide, benzalkonium chloride, cetylpyidimine chloride, cetalkonium chloride, sodium perborate, Purite, disappearing preservatives, Polyhexamethylene biguanide (PHMB), chlorobutanol, Benzododecinium bromide, "Ionic buffered system", povidone, silver, silver sulfate, betadine, and other antiseptics and proprietary and non-proprietary preservatives. The polymers herein described can be used in combination with surfactants or emulsifier. Surfactant means a chemical agent capable of reducing the surface tension of a liquid in which it is dissolved. Emulsifier means a substance which stabilizes an emulsion by increasing its kinetic stability.

An important aspect of this invention is formulations combining bi-functional copolymers with one or more preservatives, surfactants, and/or emulsifiers.

Polydispersity in these graft and block co-polymers can be either minimal or there can be significant amounts of polydispersity, and the formulations can still be effective. Viscosity can important in these formulations. Typically, with current technology, higher viscosity eye drop formulations lead to longer surface changes on an eye but are associated with visual blur and dissatisfaction by the user. There are advantages to lower viscosity agents, and in certain formulations described herein a lower viscosity can be beneficial as there will be less visual blur imparted when an eye drop is applied. In the current embodiment, the viscosity is approximately 2.7 centipoise (cP), however, it can be higher or lower. 2.7 cP is lower than the viscosity of most commercially available artificial tears. In some embodiments a higher viscosity formulation may be preferred, however. Viscosity can be adjusted by adjusting concentrations of the graft and/or block co-polymers, or by adjusting other excipients to affect viscosity. Useful viscosities are in the range of 1 cP up to and including 100 cP or higher, but typically the viscosity would be between 2 and 30 cP.

Additional exemplary components which can also be incorporated into pharmaceutical formulations and coatings for use in the present invention include, but are not limited to PLURONIC gelling agents such as, but not limited to F127, F108 as well as additional PLURONIC agents listed supra. Furthermore, in one embodiment, these components are used at fractions below that required for gelling activity.

Other components (either active or inactive ingredients) which can be included in these pharmaceutical formulations include, but are not limited to, lipids, oils, surfactants, water, lubricating polymers, typical surfactants, buffers, salts, physiologic ions, proteins, topical emollients, excipients typically used in oral, topical, mucosal, dermatologic and ophthalmic formulations, lubricants such as PEG 400, carboxymethylcellulose, hydroxypropyl methylcellulose, mineral oil, propylene glycol, glycerin, hypromellose, white petrolatum, polyvinyl alcohol, liposomes, mannitol, hydroxypropyl guar, dextran 70, viscoelastics, guar gum, alginates, and hyaluronic acid, as well as combinations thereof. Specifically, the use of the herein described copolymers for ophthalmic indications in combination with active agents described in the OTC Monograph 21CFR349.14 is claimed. Additional ingredients may include those routinely included in shampoos, soaps, and conditioners. Such components may be included in the formulations in varying percentages ranging from less than 0.1% to 99% w/w %, more preferably less than 1% to 10% w/w %. These are wt %'s relative to the total formulation.

Other components which can be included in these pharmaceutical formulations include preservatives such as, but are not limited to, Polixetonium, polyquaternium-42, Polyquaternium-1, Polyquat, Alkyl-hydroxy benzoate preservatives, parabens, hydrogen peroxide, benzalkonium chloride, cetylpyidimine chloride, cetalkonium chloride, sodium perborate, Purite, disappearing preservatives, Polyhexamethylene biguanide (PHMB), chlorobutanol, Benzododecinium bromide, "Ionic buffered system", povidone, silver, silver sulfate, betadine, and other antiseptics and proprietary and non-proprietary preservatives. Also, PLL-g-PEG, or other cationic components of graft or block co-polymers may act as a preservative. Included in this invention, also, is the use of cationic moieties in the graft or block co-polymers to serve as a preservative for a formulation containing these agents. Poly (L) lysine, alone, not coupled with a second polymer, as an ophthalmic preservative, for example, is included as an invention in this filing.

Further, in some embodiments, the formulations and coatings may include one or more additional active pharmaceutical ingredients. Examples include, but are in no way limited to anesthetics, antibiotics, anti-virals, anti-inflammatory agents, intraocular pressure lowering agents, artificial tears, lubricating products, dilating agents, immunosuppressives, anti-angiogenic agents, proteins, peptides, neuroprotectants, small molecules, growth factors and antibodies. By active pharmaceutical ingredient or API it is also meant to be inclusive of genes and/or gene transfer agents such as adenovirus, AAD and non viral vectors for which transfer and transfection is enhanced via formulations of the present invention. Formulations may be used in accordance with the present invention to deliver an active pharmaceutical ingredient which acts locally at the surface or in the tissue to which it is delivered. Alternatively, or in addition, formulations may be used in accordance with the present invention to deliver an active pharmaceutical ingredient which is then absorbed through the tissue and has a systemic or distal effect. In some embodiments, delivery of the active pharmaceutical ingredient is facilitated by external energy such as, but not limited to, iontophoresis, sonic energy, heat, microneedles, micropore creating devices such as lasers or high pressure gas.

Pharmaceutical formulations are a composition suitable for internal, topical, or ocular administration to an animal, including humans. The carrier is a pharmaceutically acceptable excipient in which the co-polymer is admixed.

"Eye lubricant" can be defined as the API included in artificial tear products based on the FDA OTC monograph 21 CFR 349.14 for ophthalmics.

pH of formulations of the present invention is in a physiologic range depending upon the site of administration and the site of the biological surface or membrane that is to be modified. Typically, the pH is above 3, e.g., above 5.6 and below 9. The pH is preferably between 6.5 and 8. Hypertonic and hypotonic formulations are claimed.

The ability of a pharmaceutical formulation comprising a graft or block co-polymer with a positively charged or hydrophobic moiety and a hydrophilic moiety to change wettability and adhere to and lubricate and modify a biological surface was demonstrated. Thus, the triboloogical properties of the surface was modified. Importantly, these formulations may have very low viscosity (lower than most artificial tear products on the market). For example, the formulation tested in humans had a viscosity of 2.7 cP. Thus, the results are not due to a simple mechanical thickening of the tear film.

Figure 2:
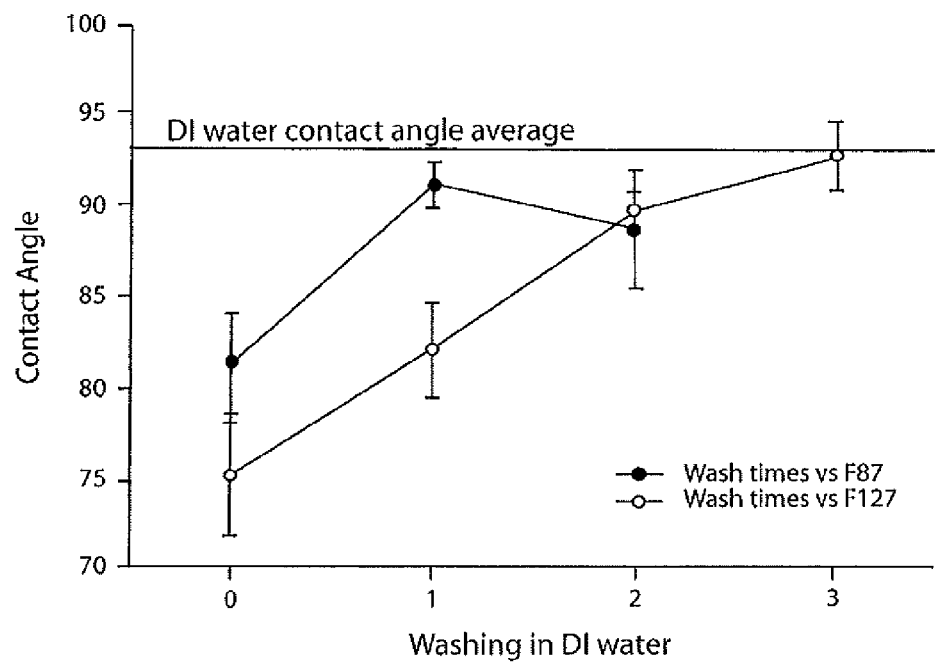
FIG. 2 shows results from an in vitro assessment of the ability of exemplary formulations of the present invention containing F87 or F127 to decrease contact angle of water to polystyrene. Formulations contained either 1% F127 (open circles) or 1% F87 (closed circles) and were compared to the average contact angle of deionized water (straight line).

The ability of formulations comprising either the graft co-polymer PLL-g-PEG or the block co-polymer F127 to change wettability was demonstrated in vitro via contact angle, experiments, as described in Example 2. FIG. 1 and FIG. 2 demonstrate the ability of exemplary formulations comprising either 1, 0.5 or 0.1% weight/weight PEG-PLL or 1% F87 or F127 weight/weight, respectively, to decrease the contact angle of water as compared to a control of deionized water. The ability of these formulations to decrease contact angle is indicative of their ability to adhere to negatively charged surfaces such as biological surfaces and/or membranes and change wettability of the biological surface and/or membrane. Through the understanding of one skilled in the art, these formulations will thus also impart surface modifications such as steric stabilization on the tissue to which the bi-functional co polymers adhere.

As described in Example 3, Ex vivo experiments in porcine eyes also showed a delay in pre-corneal water evaporation rates of approximately 2 seconds longer compared to a control of Systane® lubricant eye drops (Active Ingredients: Polyethylene glycol 400 0.4% and propylene glycol 0.3%. Inactive Ingredients: boric acid, calcium chloride, hydroxypropyl guar, magnesium chloride, potassium chloride, purified water, sodium chloride, zinc chloride.

As described in Example 1, experiments in a rabbit model also showed lack of toxicity, in other words, safety, for a formulation comprising 1% glycerin with 1% PLL-g-PEG and 1% F127 as delivery of such formulation of the present invention to a sensitive mucosal surface showed no visible irritation in the Draize test and no histopathological changes (14 day histopathology study).

Furthermore, as described in Examples 4 and 5, performance of these block and graft copolymer formulations was assessed in the eyes of human volunteers. Initial informal tolerability studies showed the eye drop was well tolerated. For example, of the multiple initial human exposures, there was no irritation or discomfort seen or reported in any subject. Additionally, there were no reports of blur following instillation of 50 microliters or less. Actually, the eye drop was described as soothing on several occasions. As a further safety step, one volunteer received 1 milliliter of solution in the eye, multiple times, and there was no irritation or discomfort. The ability to treat dry eye was then assessed using tear film break up time (TFBUT). TFBUT is indicative of the rate of evaporation of tears from the surface of the eye. The longer the TFBUT, the wetter the eye between blinks and the less likely a patient will have dry eye signs and symptoms. The first assessments were informal and performed in only a couple of subjects, then a larger masked, randomized controlled study was carried out. Administration of a formulation comprising 1% glycerin with 1% PLL-g-PEG and 1% F127 resulted in prolongation of TFBUT. In the first informal studies, the TFBUT was measured using fluorescein staining. The TFBUT was prolonged versus active comparator on one occasion at early time points, and that increase was maintained for three hours. Subjective observation of the tear film break up into smaller patches was confirmed via a non-invasive wavescan of the tear surface. The larger, randomized controlled trial studied three groups of patients (none/mild dry eye, mild/moderate dry eye, and moderate/severe dry eye). The total number of subjects was 18. Sixteen were analyzed with a noninvasive TFBUT assessment tool called the Tearscope™. In this study, there was statistically significant prolongation of the TFBUT at the 15 minute time point and the two hour time point versus active comparator (a leading OTC dry eye artificial tear). The two additional subjects underwent wavescan assessments as an alternative to the Tearscope Plus™ the results in these two subjects also showed prolongation of the tear film compared to control. Accordingly, one embodiment of the present invention relates to use of these pharmaceutical formulations as lubricating opthalmic eye drops for treatment of, for example, dry eye syndrome and contact lens intolerance. As will be understood by the skilled artisan upon reading this disclosure, however, alternative ophthalmic delivery means including, but not limited to, intraocular, periocular, conjunctival, subconjunctival, transconjunctival, peribulbar, retrobulbar, subtenons, transscleral, topical gel, topical dispersion, intraorbital, intrascleral, intravitreal, subretinal, transretinal, choroidal, uveal, intracameral, transcorneal, intracorneal, intralenticular (including phakia and psuedophakia), and in or adjacent to the optic nerve, can be used. The invention can be used with polymeric and other devices for prolonged ophthalmic drug delivery. The invention can be used with depot formulation to ease the tolerance of the eye to prolonged drug exposure.

Dry eye syndrome is a common and irritating problem for approximately 60 million Americans. Five million Americans suffer from an advanced form of this condition. Dry eye syndrome can be due to a deficiency of the aqueous, lipid, or mucin component of tears. Dry eye syndrome is also related to inflammation on the surface of the eye and irregularities of the tear film components. Aging and hormonal changes can play a role. Environment, as well as contact lenses and refractive surgery, can initiate and/or exacerbate the problem.

Dry eye is treated with eye drops, punctual occlusion, and occasionally systemically administered medicine, although eye drops are the mainstay of treatment. While most eye drop treatments are available over-the-counter, there are two prescription eye drops inclusive of steroids and cyclosporine that help with dry eye. Most over-the-counter dry eye syndrome products are washed out through the lacrimal drainage system quite quickly thus rendering relief minimal. For example, in at least two studies by Alcon, Systane had a beneficial effect on tear film break up time that lasted up to 30 minutes. These studies demonstrate Systane™ is one of the longest acting over-the-counter dry eye products. The PLL-g-PEG formulation shows results improving tear film break up time beyond two hours.

Accordingly, there is need for formulations of the present invention for treatment of this condition.

Formulations can also be used in accordance with the present invention to provide for prolonged coating of the ocular surface via the multifunctional properties of the graft and/or block co-polymers. Without being bound to any particular theory, it is believed that the hydrophilic domain(s) of the block or graft co-polymer, which keep the eye lubricated and help to retain tears on the surface, are anchored at the surface of the eye (cornea and conjunctiva) for an extended period of time through primarily interaction of positively charged domain(s) on the block, graft, or backbone of the graft copolymer and secondarily through hydrophobic domains on the block, graft or backbone of the polymer with the surface of the eye through either electrostatic attraction with the negatively charged areas on the surface of the eye or hydrophobic interactions with the hydrophobic regions of the eye that play a role in dry eye syndrome. Similarly, these polymers could interact with natural mucins and be effective in adhering to mucins and/or keeping soluble mucins in the tear longer, and/or increasing the effectiveness and natural protections provided by mucins. The formulations and use of the graft and block copolymers described herein may also have beneficial effects based on the steric stabilization of biological surfaces. The protection provided may help break the vicious cycle of inflammation, cellular injury, and discomfort.

Formulations comprising a bi-functional co-polymer and an anesthetic agent such as proparacaine can be used in accordance with the present invention to prolong the anesthetic effect and/or reduce the acute corneal surface changes seen commonly in the clinic and operating room associated with decreased sensation of the cornea and a decreased blink rate. Such formulations can be applied prior to examination and/or pre-operatively, and will help maintain a more normal corneal epithelial surface. Furthermore, use of the formulation will help reduce bacterial adherence at sites of any procedures performed on the eye and will help reduce post-procedural infection.

Formulations described herein also provide a safe, non-irritating excipient for opthamological formulations with one or more additional active pharmaceutical ingredients. For example, one aspect of the invention is the use of the block and graft copolymers described herein combined with active agents for treating ophthalmic disease. Their inclusion may reduce the irritation or tachyphylaxis (associated with some eye drops), or simply provide an additional lubricating and wettable ocular surface enhancing the comfort and acceptance of eye drops. Exemplary additional active pharmaceutical ingredients for opthamological uses include, but are not limited to, lubricants and demulcents, as described supra, antibiotics (fluoroquinolones, vancomycin, cephalosporin, gentamycin, erythromycin, azithromycin, sulfa drugs, bacitracin, gatifloxacin, levofloxin, moxifloxacin, ofoxacin), acetazolamide, antazoline, aspirin, atropine, azelastine, bacitracin, betaxolol, bimatoprost, botanical drugs including zeaxanthine lutein, lycopene brimonodine, brinzolamide, carbachol, carteolol, ciprofloxacin, ofloxacin, cromalyn, cyclosporine, cyclosporine pro-drugs and cyclosporine derivatives, other immunomodulators, dapiprazole, dexamethasone, diclofenac, dipivifren, dorzolamide, epinephrine, erythromycin, fluoromethalone, flurbiprofen, gentamycin, glaucoma medications (prostaglandins, carbonic anhydrase inhibitors, epinephrine or alpha-agonists, beta-blockers), gramicidin, homatropine, hydrocortisone, hyoscine, keterolac, ibuprofen, ketotifen, latanaprost, levobunolol, levocabastine, levofloxin, lotepprednol, medrysone, methazolamide, metipranolol, naphazoline, natamycin, nedocromil, neomycin, neuroprotective agents, nonsteroidal anti-inflammatory agents, nepafanec, norfloxacin, ofloxacin olopatadine, oxymetazoline, pemirolast, pheniramine, phenylephrine, pilocarpine, povidone, prednisolone, proparacaine, scopolamine, tetracaine, steroids, sulfacetamide, tetrahydrozoline, hypertonic tears, timolal, tobramycin, travaprost, trifluridine, trimethiprim, tropicamide, unoprostone and zinc. Prodrugs and related compounds, as well as any new active pharmaceutical ingredients can be used with the block and graft copolymers here described.

Formulations comprising a graft and/or block co-polymer can also be used in accordance with the present invention with contact lens solutions, manufacturing, rewetting drops, or in pre-insertion contact lens treatments. The graft and/or block co-polymers can be used with current contact lens care solution and rewetting drop ingredients, including, but not limited to, water, preservatives, NaCl and other salts and mineral ingredients, buffers, and other polymers and osmotic agents. The use of these graft and block co-polymers in contact lens related consumer products to impart clinical benefits is claimed. Also claimed is the use of these graft and block copolymers in the manufacture, coating, finishing, and storage of contact lenses.

Formulations comprising a bi-functional co-polymer can also be used in accordance with the present invention with a second eye drop, such as a lipid or oil based eye drop, to enhance the efficacy of the second eye drop. In one embodiment of this use, the formulation described herein is administered first followed by administration of the second eye drop.

Additionally, these formulations with the ability to prevent or inhibit cell adhesion are useful in preventing or inhibiting the spread of bacterial or viral infections such as bacterial (including Chlamydial, gonorrheal, *Staphylococcus epidermidis, Streptococcus pyogenes, Streptococcus pneumonia, Neisseria meningitidis* and *Moraxella lacunata, Haemophilus* and family Enterobacteriaceae, *Clostridium* species, gram-negative *anaerobic bacilli,* and *Peptostreptococcus* species, *N gonorrhoeae, C trachomatis,* staphylococcal species and *S pneumonia*) or viral keratitis or conjunctivitis (including herpetic keratitis and adenovirus conjunctivitis) and in preventing and/or inhibiting inflammation caused by adherence of inflammatory cells and proteins to the eye surface. The invention may be useful in treating or preventing amebic, protozoal, mycobacterial and other types of keratitis and conjunctivitis. There may be a benefit in treating sterile ulcers, ectasia, and corneal or scleral melts. The anti-inflammatory effect may also be due to inciting agents being kept off the corneal and conjunctival surface decreasing the inflammatory reaction. Such formulations will be particularly useful in neonatal, daycare, pediatric or family settings wherein outbreak of one individual can lead to infection of many others.

For the eye, the application of a formulation in accordance with the present invention is expected to reduce the exposure of the surface of the eye to bacterial antigens, such as those from *Staphylococcus Aureus*, and thus may provide an important part of the treatment for staph marginal disease. There also may be benefits to patients with allergic conjunctivitis including giant papillary conjunctivitis (limiting direct tissue exposure to antigens), and for patients who have had previous filtering surgery with thin ischemic blebs, as therapy with a formulation in accordance with the present invention is expected to reduce the risk of bleb related endophthalmitis. Additionally, after a corneal abrasion application of a formulation in accordance with the present invention can decrease the risk of corneal ulcer development, especially in the setting of injuries sustained from vegetable matter which predispose a subject to fungal infections. Other conditions that could be treated with formulations described with this invention include conjunctivitis and keratitis due to processes such as Moorens ulcer, Terriens marginal degeneration, ligneous conjunctivitis, toxic exposures, autoimmune conjunctivitis, and phlyectenular conjunctivitis. Use in patients with keratoprostheses is claimed. The eye drops can be used in mammals, humans, or even dogs, cats, and horses.

From experiments described herein, it is expected that formulations of the present invention will also be useful changing wettability and/or, steric stabilization, tribological properties, lubricating and/or preventing adherence of unwanted proteins and cells to other biological surfaces including, but not limited to, skin, mucous membranes and hair. These formulations can thus also be applied in accordance with the present invention to epithelial tissue of the skin, urinary, or gastrointestinal tract, mucous membrane, exposed wound surfaces, including respiratory tract mucosa, oral and nasal mucosa, vaginal mucosa, and conjunctival surfaces, and surgical and traumatic wounds and ulcerations. These formulations can serve to protect skin and other organs from foreign protein, viral, and bacterial adherence. Benefits can include reduction in rate of infection. Without being limited to any particular mechanism, it is believed that a formulation comprising a graft polymer as described above, such as PLL-PEG, adheres to the biological surface via the PLL moiety while the PEG moiety prevents and/or reduces the adherence of potentially harmful particles. Decreased adherence can be beneficial by decreasing pathogen or toxin exposure, thereby decreasing morbidity and mortality associated with these agents. For example, lower bacterial loads can decrease the severity of subsequent bacterial infection and/or exotoxin exposure, and allow the host defenses and antibiotics better opportunity to work. Decreasing viral exposure can reduce transmission rates and possibly the severity of viral infection. These formulations are useful as well against fungals and exposure to reactive proteins.

Accordingly, the formulations described herein have a wide variety of uses in accordance with the present invention.

For example, these formulations can be used in accordance with present invention in military applications to reduce soldiers' and citizens' morbidity associated with biological or biochemical warfare attacks.

These formulations can also be used in accordance with the present invention to reduce rates of methicillin-resistant *Staphylococcus aureus* ("MRSA") adherence in hospitalized patients, children, and the general population. MRSA is a growing concern in the health care setting. Reducing the adherence to the epithelial surface thereby reducing MRSA spread and severity and frequency of MRSA infections is expected to prove very beneficial. Such use is expandable to school situations, prehospital admission, nursing homes and chronic care facilities as well. It is not expected that MSRA, or other pathogens, would develop resistance to formulations of the invention.

These formulations can also be used in accordance with the present invention to reduce transmission of the common cold and influenza virus via nasal and inhalational applications in settings including, but in no way limited to, airplanes, preschools and schools, homes of affected viral individuals, as well as nursing homes and chronic care facilities. The block or graft co-polymers can be included in nasal sprays and products formulated for inhalational delivery, as is known to those skilled in the art. For example, a nasal spray would include the block or graft co-polymers and benzalkonium chloride, dextrose anhydrose, edentate disodium, microcrystalline cellulose and carboxymethylcellulose sodium, polysorbate 80, and purified water. An aerosol inhaler would include the block or graft co-polymers as well as ethanol and propellant such as propellant HFA-134a (1, 1, 1,2-tetrafluoroethane).

Important utilities of the formulations exist for children and adults with infirmities, such as immunodeficiencies, chronic disease and other chronic conditions such as cystic fibrosis, which leave the host more susceptible to routine illness.

Application of a formulation in accordance with the present invention to a wound just after injury or surgery, including, but not limited to corneal abrasions, corneal surgery such as LASIK, PRK, or other refractive or vision correction procedures, or intraocular surgery where an incision is made in the eye through sclera or conjunctiva/sclera, such as for cataract or glaucoma surgery. The formulation can be used again after cleansing, can reduce bacterial infection, and infectious wound complications. Such formulations may be particularly useful in the field in military medical operations, after an initial irrigation.

For these uses in humans, the formulation may be in the form of a lotion, gel, liquid, spray, rinse, dissolvable wafer, or glycerin bar to which water is added to solubilize the graft co-polymer or block co-polymer to make it more amenable to application. Formulations can be provided as individual or single use products or in volumes for industrial use and/or multiple use dispensers. In addition to the bi-functional co-polymer, such formulations may comprise any and all typical binders, excipients, and components found in cosmetic sprays, lotions, soaps, shampoos, cleansers, and oral, nasal, vaginal, and eye care products.

Formulations of the current invention can be delivered by eye drop bottles with a nozzle on the end (volume generally between 0.2 cc and 50 mL). The container may be single use disposable containing a volume of approximately 0.3 mL or a multi use vial containing a volume between 0.3 mL and 50 Ml. The material would be high density polyethylene or similar, and the container could be up to 500 mL for multipurpose contact lens solutions, and would have a nozzle. The solution could be stored in contact lens containers, as well.

By "eye care solution container" it is meant a container for eye care solutions that is made of high density polyethylene or similar thermoplastic or petroleum based plastics for health care use. The eye drop bottle is made from a mold or by blow, fill and seal methodology. The eye drop solution container has a nozzle for releasing smaller quantities of the solution than the total volume of the container. Eye care solution container may be single use or multi-use. The volumes for an eye care solution container range from 0.1 cc to 500 cc.

Formulations comprising a bi-functional co-polymer with a positively charged or hydrophobic moiety and a hydrophilic moiety can also be used in accordance with the present invention in the treatment of dry mouth in subjects with, for example, but not limited to, Sjogrens syndrome, or dry mouth during or post chemotherapy. Such formulations may further comprise traditional lubricants for such dry mouth conditions, such as, but not limited to, xylitol, and glycerin MouthKote.

The ability of these formulations to lubricate mucous membranes without irritation makes these formulations useful as sexual lubricants as well. Reduced transmission of HIV and other sexually transmitted diseases when a formulation is applied prophylactically on skin and mucosal surfaces in accordance with the present invention prior to exposure may be an additional, if not a primary benefit in this application.

Formulations can also be used in accordance with the present invention to protect gums in, for example, periodontal disease by reducing inflammatory cell and bacterial cell adherence to the gums. In this embodiment, these formulations may be incorporated into, for example, but not limited to, a toothpaste or mouthwash and may be combined with flavorant and/or fluoride. Formulations which reduce bacterial adherence in the mouth, and in particular the posterior tongue and throat, are also expected to be useful in treating bad breath or halitosis.

Formulations can also be used in accordance with the present invention as a preoperative shampoo to reduce bacterial adherence to hair and/or skin before surgery. Since these formulations have been found to be safe for administration to the eye, they provide a useful preoperative shampoo to remove any bacteria adhering to the eyelashes prior to eye surgery.

The ability to reduce or prevent bacterial adherence to biological surfaces such as skin and hair is expected to make these formulations useful in the treatment of chronic blepharitis as well, with or without concomitant steroids or antibiotics. Formulations described herein may be used on the eyelids and eye lashes, for treatment of medical conditions and for prophylaxis. For these embodiments, the formulation may be combined with an antiseptic or an antibiotic.

Further, the ability to reduce bacterial adherence to skin makes these formulations useful in deodorants to reduce body odor caused by bacteria that break down sweat.

Formulations can also be used in accordance with the present invention on animals, including household pets, to decrease bacterial adherence to their skin, oral cavity, or coats. In this embodiment, the formulation can be in the form of a spray, shampoo, lotion, or beverage.

Other uses for these formulations will become evident to those skilled in the art upon reading this disclosure and are such uses are encompassed by the present invention.

The present invention also provides coatings comprising a graft co-polymer with a positively charged or hydrophobic moiety and a hydrophilic moiety or a block co-polymer with a positively charged or hydrophobic moiety and a hydrophilic moiety for extraocular devices such as contact lenses, glaucoma stents and valves, scleral buckling hardware and external drug delivery devices. External drug delivery devices can include biodegradable devices as well as permanent products such as those made of silicon and other non bioerodible polymers. There is a potential use for intraocular devices including, but not limited to, intraocular lenses, intraocular contact lenses, glaucoma stents, tubes and valves, intracorneal implants that can be used for the correction of presbyopia, intraocular pressure sensors (including devices for continuous or microchip measurements with or without telemetry for intraocular pressure and intracranial pressure monitoring), and microchips used for retinal vision enhancement. Such coatings improve wearability and biocompatibility of these extraocular devices (such as contact lenses) and decrease proteinaceous, bacterial, fungal, and particulate adhesions to these extra-ocular devices. These coatings also improve optical performance of the lenses. Coating intraocular and extraocular devices in accordance with the present invention also reduces epithelial adhesion and fibrosis thereto.

For example, contact lenses are often difficult to tolerate due to the discomfort caused by the adhesion of proteins such as lysozyme and denuded protein products and other particles to the negative charges of the lens surface. Other particles adhering to the lens surface include bacteria and bacterial proteins, endotoxins, antibodies, calcium, and lipids. Other uncharged particles, and even negatively charged particles can build up on the lens surface once this cascade of protein adhesion, cellular and/or particulate adhesions to the lens is initiated. Wearing of contact lenses with these materials adhered to the contact lens can lead to discomfort, allergic reactions, ocular irritation, foreign body sensation, epithelial breakdown and dysfunction, and bacterial keratitis.

By binding the surface of a contact lens with positively charged and/or hydrophobic domains of block or graft co-polymers included in topical formulations of the present invention, the aggregation of protein deposits during wear time on the lens is and will be reduced and contact lenses are and will be better tolerated. The lens surface is also more lubricious, and the steric stabilization as well as high surface water retaining capacity and charge neutrality can impart numerous benefits in this clinical setting. With protection provided by the polymers herein described, the contact lenses may also be more wettable and feel more comfortable with the concomitant use of formulations described herein as well as other ophthalmic products. Formulations can be provided in accordance with the present invention as eye drops to improve contact lens wearability, as a finishing rinse after lens manufacture, in storage solutions, in lens cleaning solutions, in rewetting drops, as a drop to be used prior to placing the lens in the eye, and/or as an active preservative in contact lens preparation and storage. These formulations thus may be used in accordance with the present invention in the form of a one time application or repeated application. Contact lenses and intra- and extra-ocular devices can be made more biocompatible with the coatings of the graft and block co-polymers as described herein.

There are well known similarities, and there exists an established clinical relationship between dry eye syndrome and contact lens intolerance. In studies described in examples 4 and 5 in this invention, it has been shown clinically that the formulations and uses of graft and block copolymers described herein conferred meaningful and measurable benefit in dry eye subjects. These results are highly suggestive of a significant opportunity for clinical benefit in the contact lens use and contact lens intolerance clinical setting. By way of interpolation, it follows that there will be similar benefits conferred in the use of these graft and block copolymers on other extraocular- and intra-corneal devices.

It can be foreseen that some intra-corneal or extra-ocular devices will have prolonged biological use (for example extended wear contact lens, and surgically implanted devices). Under conditions of high stress (such as ionic, salts or other electrolyte media, enzymatic, pH, or temperature) and likely prolonged time in aqueous electrolyte media, the electrostatic or hydrophobic interactions between the graft and block copolymers and the intra- or extra ocular devices may be reduced to some degree. Additionally, the tear film, sub-epithelail, or intraocular fluid will likely not (unless a specific intervention has been undertaken for that purpose) be a reservoir for replacement graft copolymers as they naturally degrade over time. The benefit conferred by the polymers to the device may, therefore, wear off over time. Thus, there may be advantages to covalently immobilizing the block or graft copolymers herein described to the intra or extra ocular device during manufacturing or finishing. It follows, therefore, that covalently bonding, embedding during manufacture, or covalently immobilizing these graft and block co polymers to the devices may be beneficial. It has been shown that covalent immobilization does not necessarily result in less efficient packing of a graft co-polymer (Blattler, et al. Langmuir 2006, 22, 5760-5769). An aldehyde plasma polymer interlayer with reductive amination can be used in such a setting. Other methods for covalently immobilizing the block or graft copolymers can also accomplish the same result of developing a more stable and resistant coating on the surface of the device.

Use of block or graft co-polymer containing formulations to coat intracorneal devices also reduces particulate, cellular, epithelial, and/or fibrocyte adhesion. Intracorneal inlays, may benefit from the use of these graft and block copolymers. Reductions in the risk of infection and clotting or blockage by protein or fibrin debris, cellular proliferation, inflammation suppression, and steric repulsion are all ways in which these polymers may confer advantages to extra- or intraocular devices, including intracranial implants.

The descriptions provided above are not to be construed as limitations of the present invention and its various embodiments described herein, but rather, are described to fully allow one skilled in the art to make and use the invention along with modifications, adaptations, and alterations, all being within the spirit and broad scope of the present invention as fully defined herein. Similarly, the following nonlimiting examples are provided to further illustrate the present invention. Percentages are weight percents.

EXAMPLES

Example 1

The following topical formulation was made and tested:
1% F127
1% PLL-g-PEG
1% glycerin
sterile water for injection
sodium phosphate buffer
mannitol to adjust osmolality;
pH between 6.5 and 7.5 and osmolality 274-350 mOsm/kg;
Sterile Filtration This formulation was tested in the Draize test and no ocular irritation was observed.

This formulation was also tested in two volunteer humans and no irritation was reported. Tear film break up time in one volunteer was extended compared to the control eye for over two hours after instillation of the eye drops. On close inspection under microscopy, after instillation, the tear film of the eye treated with the PLL-g-PEG formulation displayed a more stable tear film. This stability was present at greater than three hours after eye drop instillation. Furthermore on analysis using a Tearscope to evaluate the tear film, compared to an eye that received a commercially available product, the eye treated with the PLL-g-PEG polymer showed an increase in tear film break up time by 30 seconds compared to control, on one occasion, at one hour after instillation of the eye drops.

This formulation was also applied to a contact lens and tested. One drop was placed on each side of a contact lens. The lens was placed in a human eye and the patient wore the contact lens comfortably for 8 hours. The treated lens was described as being more comfortable in the eye than an untreated control lens. This formulation was also mixed 1:1 with a commercially available preserved multi-purpose contact lens solution and the lens was stored in the solution overnight. The lens was worn the next day comfortably. Again, the treated lens was more comfortable than an untreated control lens. One embodiment of the copolymers herein described has thus been used as an eye drop, used in combination with other polymers, used with contact lenses, and formulated with a preservative. The subject felt decreased awareness of the contact lens and less resistance and discomfort when blinking.

Example 2

An in vitro assessment was made of the ability of 1%, 0.5%. and 0.1% PLL-g-PEG formulations and 1% formulation of F127 and F87 to decrease contact angle of water on a polystyrene surface. The contact angle of a drop of these had a much lower contact angle on a freshly cleaned polystyrene surface compared to a drop of deionized water. This experiment demonstrates the ability of these formulations to change wettability and adherence to negatively charged surfaces such as the eye and epithelium.

Example 3

An ex vivo assessment in porcine eyes was made of the ability of a PLL-g-PEG formulation of the present invention to decrease evaporation. Porcine eyes were obtained fresh and refrigerated. They were stored in an oil bath, which caused changes to the epithelial surface and also partially denuded the epithelial surface allowing for faster evaporation of an aqueous solution. The evaporation rates of small areas were measured and Systane was applied with no change in evaporation rate after a single rinse. A single rinse with the PLL-g-PEG formulation showed a reduction in evaporation time by a mean of two seconds. Five eyes were tested. The formulation was: 1% F127, 1% PLL-g-PEG, 1% glycerin, sterile water for injection, sodium phosphate buffer, mannitol to adjust osmolality.

Example 4

Two tests were performed in human eyes with a PLL-g-PEG formulation of the present invention.
The formulation was: 1% F127, 1% PLL-g-PEG, 1% glycerin, sterile water for injection, sodium phosphate buffer, mannitol to adjust osmolality.
The first involved the time a human eye could be held open before the need to blink based on discomfort. The longer an eye could be held open without pain implies a better tear film covering over time. In this experiment, one eye received a single eye drop of Optive™ while the other eye received a single eye drop of the PLL-g-PEG formulation eye drop. The control eye could be held open 30 seconds after instillation without discomfort repeatedly at most time points (every 10 to 15 minutes) from t=5 minutes to t=120 minutes. The eye treated with the PLL-g-PEG formulation could be held open without discomfort for times ranging from 40 to 60 seconds at most time points.

The tear film was also assessed by Fluorescein tear film break up time. At t=200 minutes after instillation, there was a longer time to TFBUT by at least 5 seconds in the PLL-g-PEG treated eye. Additionally, the break up occurred with a much smaller area of change on the surface of the eye. These results were confirmed subjectively with the wavescan device looking at tear film reflectance of light and aberrations.

Example 5

The formulation was: 1% F127, 1% PLL-g-PEG, 1% glycerin, sterile water for injection, sodium phosphate buffer, mannitol to adjust osmolality.

A randomized, masked, active comparator controlled study was carried out in eighteen subjects. The study endpoints included subjective response to the eye drops and the tear film break up time compared to preinstillation values at t=15, 30, 60, and 120 minutes. Noninvasive tear film break up time (NIBUT) was performed using the Tearscope™ in 16 subjects; fluorescein break up time (FBUT) at 120 minutes was also measured in these sixteen subjects. Two subjects were tested with wavescan techniques to look at tear film break up time with that new technology. A questionnaire was administered to subjectively assess the acceptability of the eye drops in all subjects. The principal investigator was not affiliated with the product and is a full professor at an academic eye institute. The principal investigator was responsible for the trial. IRB approval was obtained, and the trial was registered at clinicaltrials.gov, as per FDA requirements. The comparator was a leading over-the-counter product with the following formulation: Active Ingredients: Polyethylene glycol 400 0.4% and propylene glycol 0.3%. Inactive Ingredients: boric acid, calcium chloride, hydroxypropyl guar, magnesium chloride, potassium chloride, purified water, sodium chloride, and zinc chloride. In the Tearscope portion with sixteen subjects, three groups were studied: the first group of five subjects had none, occasional, or mild dry eye symptoms. The second group of five subjects had mild to moderate dry eye symptoms. The third group of six had moderate to severe dry eye symptoms. RESULTS: Questionnaire: there was no difference overall between the acceptance of the eye drops. See Table 1.

TABLE 1

| Preferred at 5 minutes after instillation | |
|---|---|
| Sample formulation | 4 |
| Active comparator | 5 |
| No difference | 7 |

Figure 3:
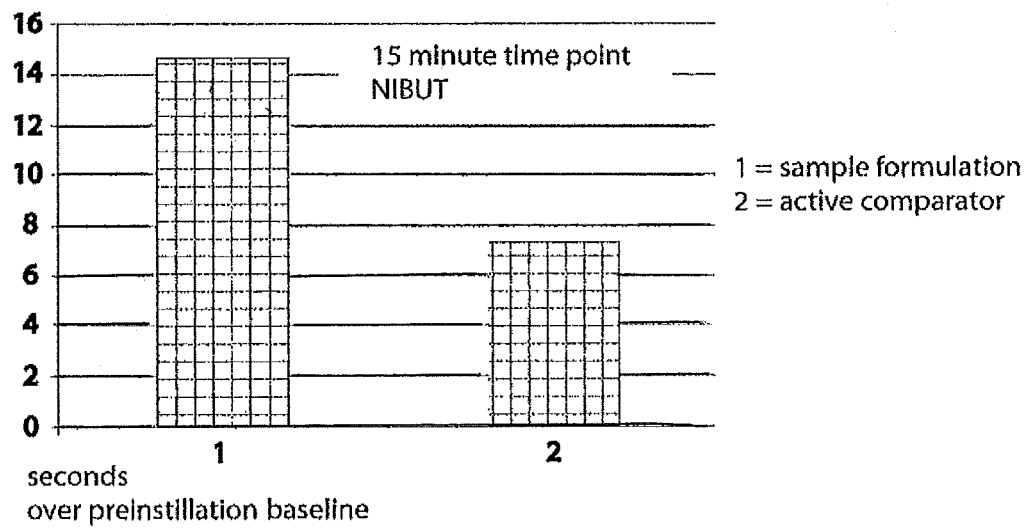
FIG. 3 shows the results of a randomized, controlled, double masked clinical trial in sixteen subjects where the tear film break-up time was measured at varying time points after eye drop instillation. This clinical methodology is a common assessment tool for dry eye syndrome, as well as to determine the effectiveness of artificial tears. Fifteen minutes after instillation of sample formulation and active control, sample formulation showed extension of noninvasive tear film break-up time from baseline of 14.67 sec (p=0.05), while active comparator was 7.4 seconds longer than baseline (p=0.34).
Figure 4:
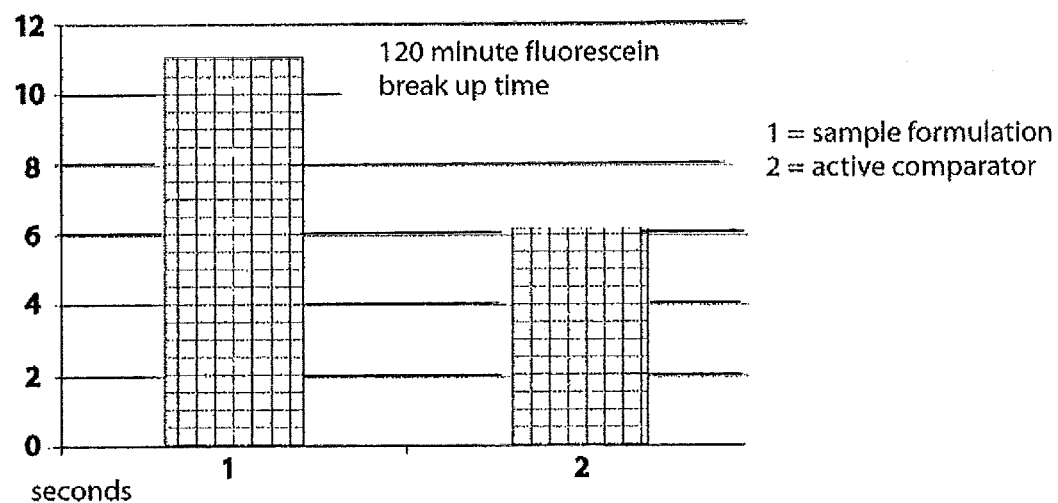
FIG. 4 shows results from the same randomized, controlled, double masked clinical trial where the tear film break-up time was measured at varying time points in subjects. Fluorescein break-up time was longer than active comparator at 120 minutes; superior by 4.92 sec (p=0.12).

Vision changes: No change: 100% Eyeon; No change: 87.5% (2 said vision was blurrier after active comparator was received. Comments at two hours if any: Equivalent for active comparator and study formulation. Regarding slit lamp exam, there were no adverse events in any eyes, and there were no changes in the anterior segment exam in any eyes. NIBUT results for the entire cohort: 15 minute time point showed NIBUT time increase from baseline at plus 14.67 sec (p<0.05) for sample formulation, while active comparator was 7.4 seconds longer than baseline (p=0.3). Thus, the new formulation essentially doubled the tear film break up time benefit of the active comparator at 15 minutes. FBUT was significantly longer than active comparator at 120 minutes; superior by 4.92 sec (p<0.12). See FIGS. 3 and 4.

The two subjects who had wavescan evaluation showed results that supported the conclusions in the larger study, for example, the mean TFBUT was longer for the sample formulation than active comparator at all time points.

Figure 5:
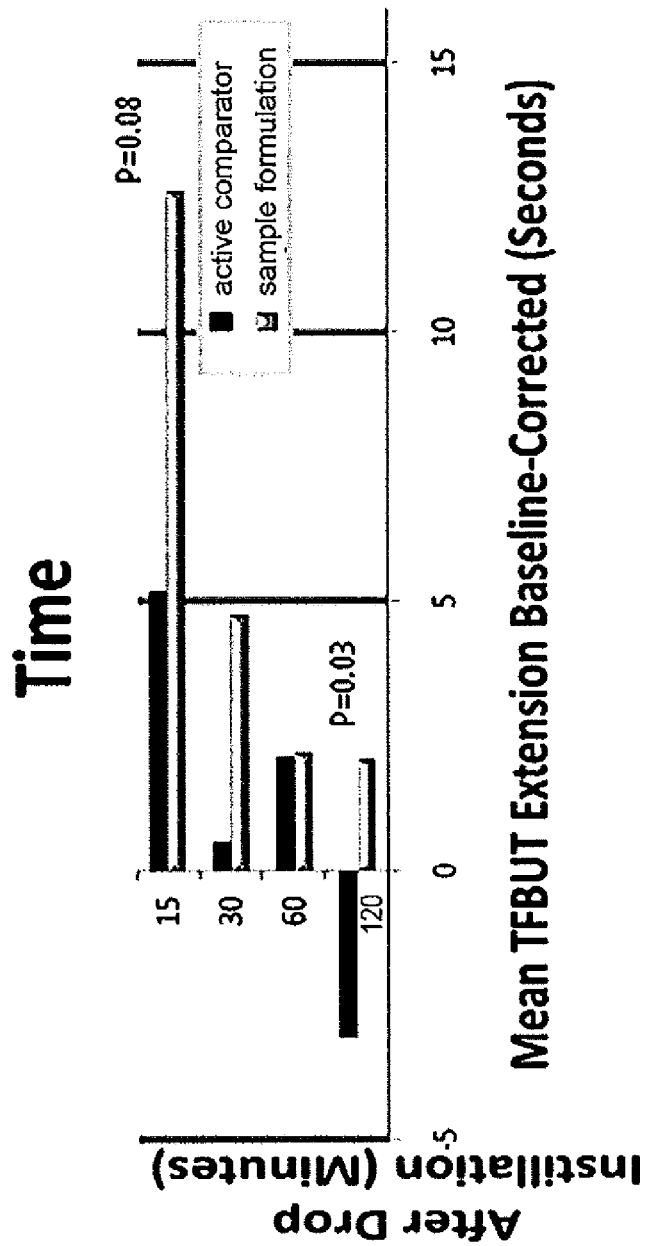
FIG. 5 shows results of a sub group analysis of the trial described above. In the main group of 16 subjects in the trial, there were three subjects that had unexpectedly long pre-instillation TFBUT. These long initial values distorted the relative contributions of the artificial tears to NIBUT for the other subjects. When these three outliers were removed, there was superiority in extending NIBUT for the sample formulation at every time point. The data is graphed based on extension by seconds over baseline in FIG. 5.
Figure 6:
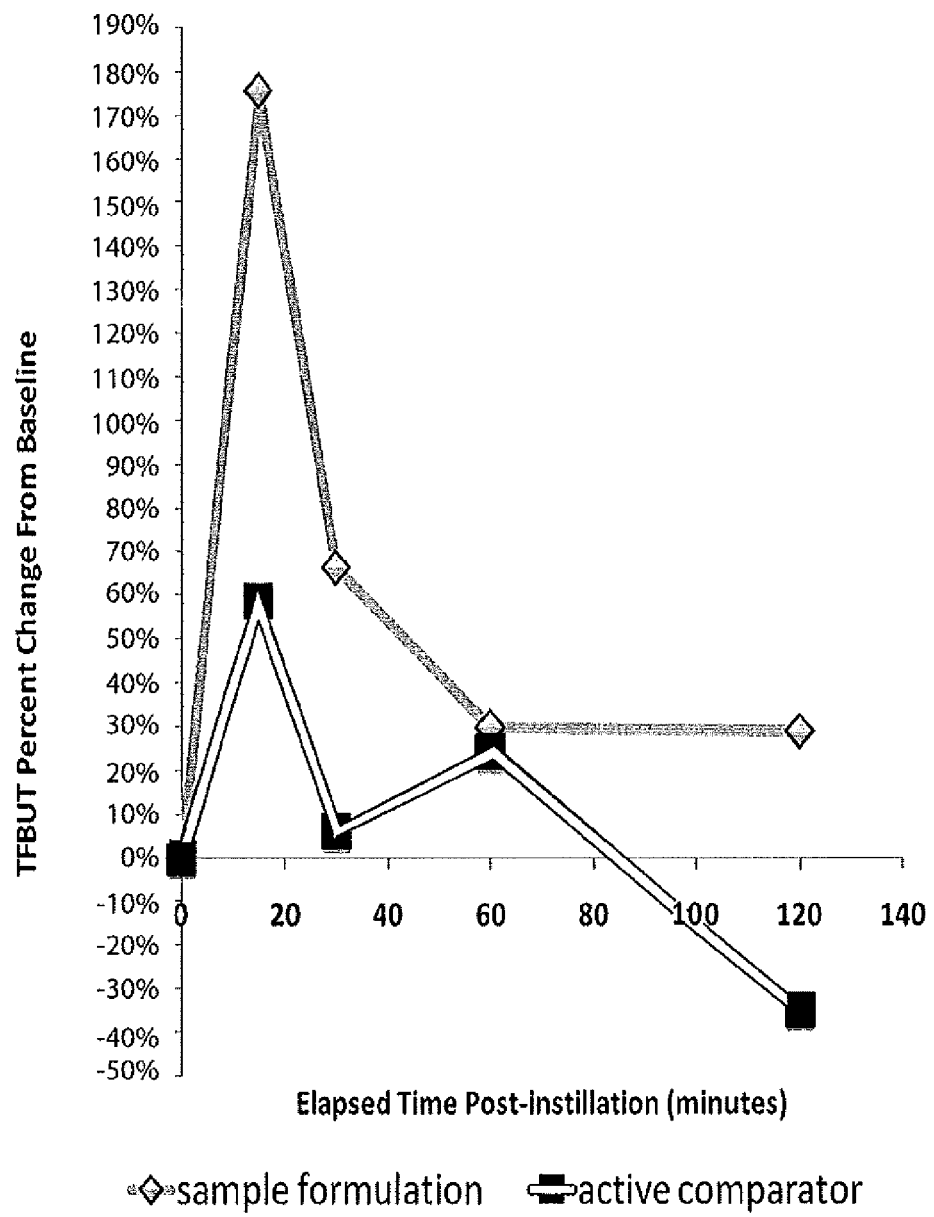
FIG. 6 shows results of a sub group analysis of the trial described above similar in method to FIG. 5. In the main group of 16 subjects in the trial, there were three subjects that had unexpectedly long pre-instillation TFBUT. These long initial values distorted the relative contributions of the artificial tears to NIBUT for the other subjects. When these three outliers were removed, there was superiority in extending NIBUT for the sample formulation at every time point. The data is graphed by percentage change from baseline in FIG. 6.

Furthermore, a sub group analysis was performed. In the main group of 16 subjects there was one subject in each group that had unexpectedly long pre-instillation TFBUT. These long initial values distorted the relative contributions of the artificial tears to NIBUT for the other subjects. When these three outliers were removed, there was superiority in extending NIBUT for the sample formulation at every time point. The data was evaluated by seconds over baseline, and by percentage change from baseline. See FIGS. 5 and 6.

Thus, this randomized, controlled, masked trial supports use of the invention for treatment, including prevention, of dry eye, contact lens intolerance, ocular irritation, and other disorders of the skin and mucous membranes.

Example 6

There is a need for compositions for treating injuries that can be custom loaded with therapeutic agents based on the suspected bacterial species in a wound on an external body surface (e.g., the skin). Non-restrictive loading could potentially reduce bacterial colonization by orders of magnitude and reduce infection rates in compromised patients with contaminated wounds. The following results indicate that compositions containing a copolymer having a positively charged, or hydrophobic, or covalent bonding moiety and a hydrophilic moiety are useful as a carrier for antibiotics. Such compositions may be used alone, as an adjunctive therapy to wound treatment, or to protect against pathogen or toxin attack (e.g., from bacterial infection).

A composition containing a copolymer having a positively charged, or hydrophobic, or covalent bonding moiety and a hydrophilic moiety is formed into a wound management device or formulated in a pharmaceutical composition. The copolymer composition is tested on a mouse model of wound healing. Mice treated with the copolymer composition have faster and/or more complete wound healing compared to untreated mice. Mice treated with the copolymer composition also have fewer or less bacterial infection compared to untreated mice.

The copolymer composition is loaded with the antibiotic amikacin. Amikacin release from the copolymer composition is measured. The open wounds of the mice may be passively or actively infected with bacteria. Bacterial growth inhibition of *P. aeruginosa* is observed for wounds treated with the copolymer composition. Treatment of wounds with a copolymer composition with antibioitics results in inhibition of bacterial growth and progress in wound healing compared to mice treated with the copolymer composition alone or with no treatment.

The ability to customize the antibiotic choice is advantageous because it allows clinicians to tailor treatment regimens based on known or suspected bacterial species present. Copolymer compositions of the invention allow for high release concentrations of antibiotics. These experiments indicate that incorporation of antibiotics into a copolymer composition provides a local drug delivery system that can be used alone or in conjunction with wound treatment therapies.

Example 7

There is a need for nanoparticle compositions for treating onasal and inhalational conditions that can be custom loaded with active or therapeutic agents based on the treatment required. Nanoparticles coated with a copolymer having a positively charged, or hydrophobic, or covalent bonding moiety and a hydrophilic moiety can be used to deliver active or therapeutic agents for inhalational applications. For inhalation, the nanoparticle size should be 10 microns or smaller in diameter, about 1 micron or less in diameter. The copolymer coated nanoparticles are formulated with a pharmaceutically acceptable carrier. The copolymer coated nanoparticles can be used in a pharmaceutical composition that is administered to the oral, nasal, or respiratory surfaces (e.g., in the throat) using an aerosol or nasal formulation (e.g., a spray). The copolymer coated nanoparticles contain active or therapeutic agents, including drugs (e.g., an antibiotic), menthol, or other numbing compound for treatment of coughs or sore throats. The copolymer coated nanoparticles deliver the active and therapeutic agents when contacted to oral, nasal, or respiratory surfaces (e.g., mucous membranes). Thus, the copolymer coated nanoparticles are used to deliver active and therapeutic agents.

The invention claimed is:

1. A method for prolonging the stability of an ocular surface tear film of a subject, comprising:
    contacting said ocular surface of said subject with a composition comprising a graft copolymer having
    a) a positively charged backbone; wherein the positively charged backbone is selected from the group consisting of poly(aminoethyl methacrylate) homo- and co-polymers containing N,N dimethylaminoethylmethacrylate repeat units, poly(trimethylammonioethyl methacrylate chloride), poly-(2-(dimethylamino) ethyl methacrylate) (pDMAEMA), poly-(2-(dimethylamino) ethyl methacrylatecomethacrylic acid) (pDMAEMA-co-MAA) and poly-(2-methyl-acrylic acid 2-[(2-dimethylamino-ethyl)-methylamino]-ethyl ester) (pDAMA), and cation guar gum, and
    b) one or more hydrophilic water soluble side chains selected from the group consisting of polyethylene glycols, polysaccharides, poly(meth)acrylates, polyacrylamides, polyvinyl alcohol (PVA), polyethyloxazoline, poly-N-vinyl pyrrolidone (NVP) and poly boronic-based polymers,
    in an amount and for a duration so as to prolong the stability of said tear film of said subject.

2. The method of claim 1 wherein said graft copolymer creates a covalent linkage between said graft copolymer and said ocular surface.

3. The method of claim 1, wherein said graft copolymer creates an electrolytic interaction between said graft copolymer and said ocular surface.

4. The method of claim 1, where said polyethylene glycols are selected from the group consisting of polyethylene glycol, polypropylene glycol, and mixtures thereof.

5. The method of claim 1, where said polysaccharides are selected from the group consisting of dextran, carboxylated cellulosics, carboxymethyl cellulose, natural gums, carageenan, alginates and hyaluronic acid and mixtures thereof.

6. The method of claim 1, where poly boronic based polymers are selected from polymers having boronic-based functional groups selected from the group consisting of:
a) phenylboronic acid (PBA), 2-carboxyethaneboronic acid, 1, 2-dicarboxyethaneboronic acid, ββ'-d carboxyethaneboronate, βγ-dicarboxypropaneboronate, 2-nitro- and 4-nitro-3-succinamidobenzene boronic acids, 3-nitro-4-(6-aminohexylamido)phenyl boronic acid, {4-[(hexamethylenetetramine) methyl]phenylboronic acid, 4-(N-methyl)carboxamidobenzene boronic acid, 2-{[(4-boronphenyl)methyl]-ethylammonio} ethyl and 2-{[(4-boronphenyl) methyl]diethylammoniol-ethyl groups, succinyl-3-aminophenylboronic add, 6-aminocaproy 1-3-aminophenylboronic acid, 3-(N succinimidoxycarbonyl) aminophenyl boronate, p-(.omega.-aminoethyl)phenylboronate, p-vinyl benzeneboronate, N-(3-dihydroxyborylphenyl)succinamic acid, N-(4-Mtro-3-dihydroxyborylphenyl)succinamic acid, O-dimethylaminomethylbenzeneboronic acid, 4-carboxybenzeneboronic acid, 4-(N-octyl) carboxamidobenzeneboronic acid, 3-nitro-4-carboxybenzeneboronic acid, 2-nitro-4-carboxybenzene boronic acid, 4-bromophenylboronate, p-vinylbenzene boronate, 4-(.omega.-aminoethyl)phenylboronate, catechol [2-(diethylamino)carbonyl, 4-bromomethyl]phenyl boronate, and 5-vinyl-2-dimethylaminomethylbenzeneboronic acid.

7. The method of claim 1, wherein said graft copolymer comprises 0.001 to 40% of said composition.

8. The method of claim 1, wherein said composition further comprises a second polymer.

9. The method of claim 1, wherein said composition further comprises one or more of a surfactant, a preservative, and a pharmaceutical ingredient selected from the group consisting of: a demulcent, an emollient, sodium chloride and a vasoconstrictor.

10. The method of claim 1, further comprising contacting topically to said ocular surface a second, different eye drop.

11. The method of claim 9, wherein said vasoconstrictor is selected from the group consisting of Ephedrine hydrochloride, Naphazoline hydrochloride, Phenylephrine hydrochloride and Tetrahydrozoline hydrochloride.

12. The method of claim 9, wherein said emollient is selected from the group consisting of Lanolin, mineral oil, paraffin, petrolatum, white ointment, white petrolatum, white wax and yellow wax.

13. The method of claim 1, wherein prolonging said stability of an ocular surface tear film of a subject provides prolonged ocular comfort to said subject.

14. The method of claim 1, wherein said composition is in a volume sufficient for instillation in the eye, and wherein said graft copolymer is at a concentration ranging from 0.1 to 3 wt %.

15. The method of claim 1, wherein said composition further comprises a poly(ethylene oxide)-poly(propylene oxide) block co-polymer surfactant.

16. The method of claim 1, wherein said composition further comprises an active agent for treating ophthalmic disease.

17. The method of claim 16, wherein said active agent is selected from the group consisting of an antibiotic, acetazolamide, antazoline, aspirin, atropine, azelastine, bacitracin, betaxolol, bimatoprost, a botanical drug, lutein, lycopene brimonodine, brinzolamide, carbachol, carteolol, ciprofloxacin, ofoxacin, cromalyn, cyclosporine, a cyclosporine pro-drug, a cyclosporine derivative, an immunomodulator, dapiprazole, dexamethasone, diclofenac, dipivifren, dorzolamide, epinephrine, erythromycin, fluorometholone, flurbiprofen, gentamycin, a glaucoma medication, gramicidin, homatropine, hydrocortisone, hyoscine, keterolac, ibuprofen, ketotifen, latanaprost, levobunolol, levocabastine, levofloxin, lotepprednol, medrysone, methazolamide, metipranolol, naphazoline, natamycin, nedocromil, neomycin, a neuroprotective agent, a nonsteroidal anti-inflammatory agent, nepafanec, norfloxacin, ofloxacin olopatadine, oxymetazoline, pemirolast, pheniramine, phenylephrine, pilocarpine, povidone, prednisolone, proparacaine, scopolamine, tetracaine, steroids, sulfacetamide, tetrahydrozoline, hypertonic tears, timolal, tobramycin, travaprost, trifluridine, trimethiprim, tropicamide, unoprostone and zinc.

18. The method of claim 17, wherein said antibiotic is selected from the group consisting of fluoroquinolones, vancomycin, cephalosporin, gentamycin, erythromycin, azithromycin, sulfa drugs, bacitracin, gatifloxacin, levofloxin, moxifloxacin and ofloxacin.

19. The method of claim 17, wherein said glaucoma medication is selected from the group consisting of a prostaglandin, a carbonic anhydrase inhibitor, an epinephrine agonist, an alpha-agonist, and a betablocker.

* * * * *